US 9,428,519 B2

(12) United States Patent
Xu et al.

(10) Patent No.: US 9,428,519 B2
(45) Date of Patent: Aug. 30, 2016

(54) ACYLATED DERIVATIVE OF HOMOHARRINGTONINE, PREPARATION METHOD THEREFOR, AND APPLICATION THEREOF

(75) Inventors: Rongzhen Xu, Zhejiang (CN); Frank Rong, Zhejiang (CN); Fuwen Xie, Fujian (CN); Hongxi Lai, Fujian (CN)

(73) Assignee: HANGZHOU BENSHENG PHARMACEUTICAL CO., LTD., Zhejiang (CN)

( * ) Notice: Subject to any disclaimer, the term of this patent is extended or adjusted under 35 U.S.C. 154(b) by 206 days.

(21) Appl. No.: 14/239,372

(22) PCT Filed: Aug. 20, 2012

(86) PCT No.: PCT/CN2012/080361
§ 371 (c)(1),
(2), (4) Date: Jun. 6, 2014

(87) PCT Pub. No.: WO2013/023622
PCT Pub. Date: Feb. 21, 2013

(65) Prior Publication Data
US 2014/0303147 A1 Oct. 9, 2014

(30) Foreign Application Priority Data

Aug. 18, 2011 (WO) ............... PCT/CN2011/078589

(51) Int. Cl.
A61K 31/55 (2006.01)
C07D 491/147 (2006.01)
C07D 491/20 (2006.01)

(52) U.S. Cl.
CPC .......... *C07D 491/147* (2013.01); *C07D 491/20* (2013.01)

(58) Field of Classification Search
CPC ..................... A61K 31/55; C07D 491/147
USPC ..................... 514/214.01; 540/581
See application file for complete search history.

(56) References Cited

FOREIGN PATENT DOCUMENTS

| CN | 1463975 A | 12/2003 |
| CN | 101585840 A | 11/2009 |
| WO | 9948894 A1 | 9/1999 |
| WO | 2009148654 A2 | 12/2009 |

OTHER PUBLICATIONS

International Search Report for International Application No. PCT/CN2012/080361, dated Dec. 6, 2012 (4 pages).
International Preliminary Report on Patentability for International Application No. PCT/CN2012/080361, dated Nov. 18, 2013 (10 pages).
Usami et al., (2010) "Antitumor Agents. 282.2'-(R)-O-Acetylglaucarubinone, a Quassinoid from Odyendyea gabonensis As a Potential Anti-Breast and Anti-Ovarian Cancer Agent" J. Nat. Prod., 73 (9), pp. 1553-1558.

*Primary Examiner* — Brenda Coleman
(74) *Attorney, Agent, or Firm* — Brian C. Trinque; Lathrop & Gage LLP

(57) ABSTRACT

The present invention belongs to the field of natural medicine and pharmaceutical chemistry, and relates to novel homoharringtonine acylated derivatives of formula (I) and formula (II) and a pharmaceutically acceptable salt thereof, to a process for the preparation of these compounds, compositions containing such compounds and their use in preparing antineoplastic medicaments.

16 Claims, 11 Drawing Sheets

Dynamic curve of the effect of BS-HH-002 on the transplanted tumor of leukemia in NOD/SCID mice Effect of BS-HH-002 on the weight of the transplanted tumor of leukemia in NOD/SCID mice Effect of BS-HH-002 on the weight of the transplanted tumor of leukemia in NOD/SCID mice Note: * indicates p<0.05 as compared with the control group.

Inhibition of transplanted tumor of leukemia in NOD/SCID mice by BS-HH-002

Effect of BS-HH-002 on the weight of the transplanted tumor of gastric cancer in BALB/c-nu nude mice Effect of BS-HH-002 on the weight of the transplanted tumor of gastric cancer in BALB/c-nu nude mice Note: * indicates p<0.05 and ** indicates p<0.01 as compared with the control group.

Inhibition of the transplanted tumor of gastric cancer in BALB/c-nu nude mice by BS-HH-002

ACYLATED DERIVATIVE OF HOMOHARRINGTONINE, PREPARATION METHOD THEREFOR, AND APPLICATION THEREOF

RELATED APPLICATIONS

This application is a 35 U.S.C. §371 filing of International Application No. PCT/CN2012/080361, filed Aug. 20, 2012; which claims priority to International Patent Application No. PCT/CN2011/078589, filed Aug. 18, 2011. The entire contents of each are incorporated herein by reference.

TECHNICAL FIELD

The present invention belongs to the field of natural medicine and pharmaceutical chemistry, and relates to novel homoharringtonine derivatives, in particular acylated homoharringtonine derivatives, to a process for the preparation of these compounds, compositions containing such compounds and their use in preparing antineoplastic medicaments.

BACKGROUND OF THE INVENTION

Homoharringtonine (HHT), also known as O-3-[(2R)-2,6-dihydroxy-2-(2'-methoxy-2'-oxoethyl)-6-methylheptanoyl] cephalotaxine, is an alkaloid extracted and separated from Chinese herbal plants of Cephalotaxaceae family, in particular from *cephatotaxus fortuneif* or congeners thereof. *Cephatotaxus* genus plants of the Cephalotaxaceae family consist of 9 species, 8 of which are originated in China. Plants of this genus contain a plurality of alkaloids, in which harringtonine, homoharringtonine, isoharringtonine and deoxyharringtonine have been extracted, identified and extensively investigated [ZHONG Sanbao et al., Studies on Semi-synthesis of Cephalotaxine Esters and Correlation of Their Structures with Antitumor activity, *Acta Pharmaceutica Sinica*, 1994, 29 (1), 33-39; WANG Dingzhi et al., Studies on Alkaloids in *Cephatotaxus* genus Plants, *Acta Pharmaceutica Sinica*, 1992, 03, 178-184]. Furthermore, a non-ester alkaloid (i.e. cephalotacine) is also separated from *Cephatotaxus* as a main component.

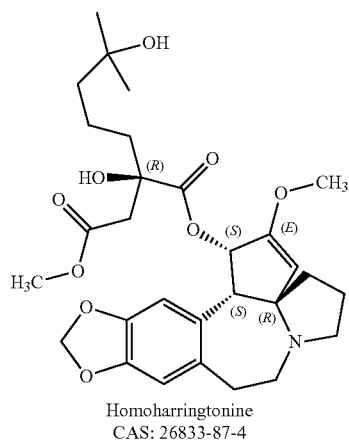

Homoharringtonine
CAS: 26833-87-4

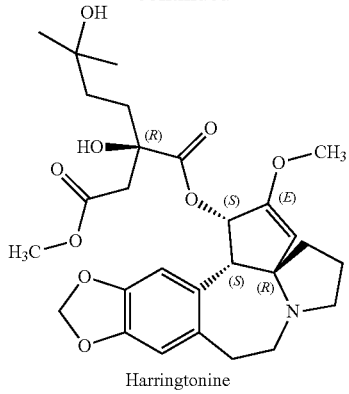

Harringtonine
CAS: 26833-85-2

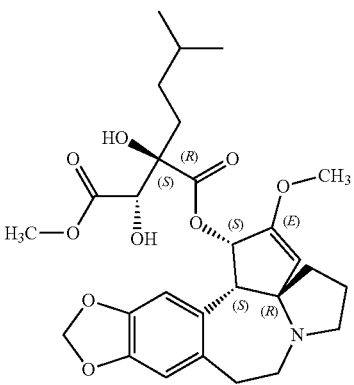

Isoharringtonine
CAS: 26833-86-3

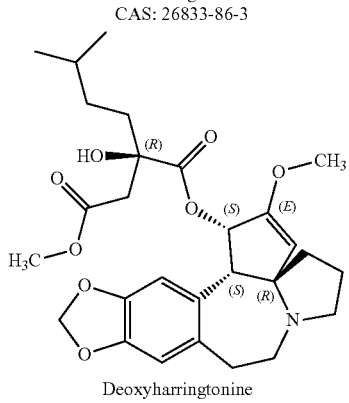

Deoxyharringtonine
CAS: 26804-95-2

Clinical studies demonstrate that HHT can be applied in the remission induction and post-remission treatment of acute myeloid leukemia, in the treatment of myelodysplastic syndrome (MDS), chronic myelogenous leukemia, polycythemia vera and malignant lymphoma, etc., particularly in the treatment of acute non-lymphocytic leukemia [ZHANG, Zhixue et al., Clinical study of HAG projects for the treatment of middle and high risk myeloid hyperplasia singular syndrome and acute myeloid leukemia, *Journal of Jinggangshan University*, 2010, 31(6), 108-110; DENG, Jianqun et al., The impact of homoharringtonine to leukemia proto-oncogene bcl-2, c-myc, tumor suppressor gene p15, *Chin J of Clinical Rational Drug Use*, 2010, 3(7), 15-16; CHEN, Lijuan et al., A Study of Apoptosis on Non-lymphocytic Leukemia Cells Induced by Cytosine Arabinoside and Homoharringtonine, *Jiangsu Medical Journal*, 1999, 25(4), 257-258; ZHANG, Hui et al., 27 clinical analysis of LD-HA regimen in the treatment of acute myeloid leukemia, *Acta Academiae Medicinae Suzhou*, 1997, 17(4), 689-690; DING, Suxin et al., 26 clinical analysis of LD-HA regimen in the treatment of hypoplastic leukemia, *Acta Academiae Medicinae Suzhou*, 1997, 17(1), 89-90; XUE, Yanping et al., Clinical observation of HAD regimen in the treatment of adult acute non-lymphocytic leukemia, *Chinese Journal of Hematology*, 1995, 16(2), 59-61].

HHT can promote cell differentiation and apoptosis [WANG Yun et al., Experimental study of K562 and CML cell apoptosis and differentiation induced by homoharringtonine, *Shanghai Medical Journal*, 2001, 24(3), 166-168; LU, Dayong et al., Effect of homoharringtonine on leukemia cell differentiation and tumor metastasis, *Journal of Shanghai University*, 1999, 5(2), 175-177].

According to the studies on the synchronous KB (human oral epidermoid carcinoma) cells, HHT possesses cell cycle specificity and has the strongest killing effect on the cells in G1 and G2 phases and a relatively weaker effect on cells in S phase [JIN, Wei et al., Studies on the effect of homoharringtonine on HL-60 cells and QCY7703 cells, *Acta Chinese Medicine and Pharmacology*, 2001, 29(3), 44-45; LUO, Chenmei et al., Effect of homoharringtonine and Xueshuantong on human pterygium fibroblasts cell cyclic variation, *Journal of Traditional Chinese Ophthalmology*, 1999, 9(2), 67-70].

The pharmacological effects of HHT are mainly in inhibiting the protein synthesis of the eukaryotic cells, inhibiting the binding of aminoacyl-tRNA to riboses and the formation of the ribosomes thereof and peptide chains, thereby affecting the early stages of polymer formation, and causing the polyribosomes to disaggregate, interfering ribosomal protein functions, and also inhibiting the synthesis of intracellular DNAs [CAI, Zhen et al., Involvement of apoptosis-related gene Survivin, bcl-2 and bax in the homoharringtonine-induced apoptosis of myelodysplastic syndrome cell line (MUTZ-1), *Journal of Practical Oncology*, 2003, 18(3), 188-191; CAI, Zhen et al., Expression of survivin mRNA in HHT-induced cell apoptosis of hematological malignancy cell lines, *Journal of Zhejiang University*, 2006, 35(2), 204-208; WANG, Hengxiang et al., Homoharringtonine Induces Apoptosis of K562 Cells through Inhibition of P210bcr/abl, *Chinese Journal of Experimental Hematology*, 2000, 8(4), 287-289; CHEN, Chunyan et al., Comparative proteomics research of apoptosis initiation induced by homoharringtonine in HL-60 cells, *Chinese Journal of Hematology*, 2003, 24(12), 624-628; LI, Yufeng et al., Effect of homoharringtonine on the telomerase activity of bone marrow CD34+ cells in patients of chronic myeloid leukemia, *Journal of Leukemia-Lymphoma*, 2004, 13(1), 42-43; LI, Yufeng et al., Effect of homoharringtonine on bone marrow CD34⁻+CD7⁻+ cells in patients of chronic myeloid leukemia, *Chinese Journal of Hematology*, 2007, 28(10), 706-707; LI, Yufeng et al., Effect of homoharringtonine on T and Th lymphocytes subsets in patients of chronic myeloid leukemia, *Leukemia-Lymphoma*, 2006, 15(1), 37-39; LI, Yufeng et al., Effect of homoharringtonine on the telomerase activity of bone marrow cells and K562 cells in patients of chronic myeloid leukemia, *Chinese Journal of Hematology*, 2003, 24(6), 329-329; MENG, Xiaoli, Effects of homoharringtonine on telomerase activity in HL60 cells, *Journal of Zhengzhou University*, 2004, 39(3), 440-442; XIE, Wanzhuo et al., Effect of telomerase in homoharringtonine-induced apoptosis of HL-60 cells, *Chinese Journal of Medical Genetics*, 2002, 19(2), 169-171]. Other applications of these harringtonine natural products are also under development. Up to now, however, reports on the synthesis and application of novel mono-acylated and di-acylated homoharringtonine derivatives have not yet been seen.

SUMMARY OF THE INVENTION

One object of the present invention is to provide novel mono-acylated homoharringtonine derivatives of formula (I) or novel di-acylated homoharringtonine derivatives of formula (II)

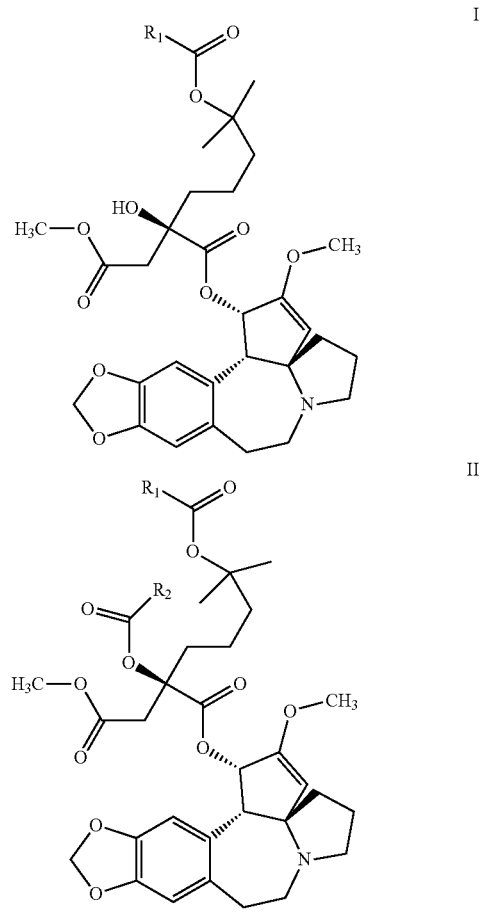

wherein $R_1$ and $R_2$ are independently selected from H, $C_1$-$C_{20}$ alkyl, $C_2$-$C_{20}$ alkenyl, $C_4$-$C_{20}$ conjugated alkenyl, $C_3$-$C_7$ cycloalkyl or cycloalkenyl, aryl, heterocyclyl, heteroaryl, and amino acid side chain residues, which, except for hydrogen, are optionally substituted with one or more substituent selected from the group consisting of halogen, amino, $C_1$-$C_6$ alkylamino, nitro, cyano, hydroxyl, $C_1$-$C_6$ alkoxy, thiol and $C_1$-$C_6$ alkylthio; said $C_3$-$C_7$ cycloalkyl or cycloalkenyl, aryl, heterocyclyl or heteroaryl are optionally substituted with $C_1$-$C_6$ alkyl, and said $C_1$-$C_{20}$ alkyl, $C_2$-$C_{20}$ alkenyl or $C_4$-$C_{20}$ conjugated alkenyl are optionally substituted with aryl or heteroaryl;

or a pharmaceutically acceptable adduct, complex or salt thereof.

Another object of the present invention is to provide a process for preparing the mono-acylated homoharringtonine derivatives of formula (I) of the present invention, comprising 1) subjecting an optionally activated homoharringtonine and an organic acid $R_1CO_2H$ to condensation esterification;

2) subjecting homoharringtonine and an organic acyl chloride $R_1COCl$ or an organic anhydride $(R_1CO)_2O$ to condensation esterification; or 3) reacting an activated organic acid $R_1CO_2H$ with homoharringtonine;

to obtain the compound of formula (I), wherein $R_1$ is defined as above for compounds of formula (I).

The present invention also provides a process for preparing the di-acylated homoharringtonine derivatives of formula (II) of the present invention, comprising 1) subjecting optionally activated homoharringtonine and an organic acid $R_1CO_2H$ to condensation esterification (wherein $R_1=R_2$) or subjecting an optionally activated compound of formula (I) and an organic acid $R_2CO_2H$ to condensation esterification;
2) subjecting homoharringtonine and an organic acyl chloride $R_1COCl$ or an organic anhydride $(R_1CO)_2O$ to condensation esterification (wherein $R_1=R_2$) or subjecting a compound of formula (I) and an organic acyl chloride $R_2COCl$ or an organic anhydride $(R_2CO)_2O$ to condensation esterification; or
3) reacting an activated organic acid $R_1CO_2H$ with homoharringtonine (wherein $R_1=R_2$) or reacting an activated organic acid $R_2CO_2H$ with a compound of formula (I);

to obtain a compound of formula (II), wherein $R_1$ and $R_2$ in each formula are defined as above for compounds of formula (II).

Another object of the present invention is to provide a pharmaceutical composition containing the compounds of the present invention, wherein said pharmaceutical composition comprises at least one compound of the present invention and optionally a pharmaceutically acceptable excipient.

Yet another object of the present invention is to provide use of the compound of the present invention or the pharmaceutical composition comprising said compound in the manufacture of a medicament, in particular an antitumor medicament. Accordingly, the present invention also provides a method for treating a subject suffering from tumor, comprising administering to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor and prostate cancer, etc.

The present invention also relates to the compounds of the present invention used for treating a tumor.

DETAILED DESCRIPTION OF THE INVENTION

Figure 1:
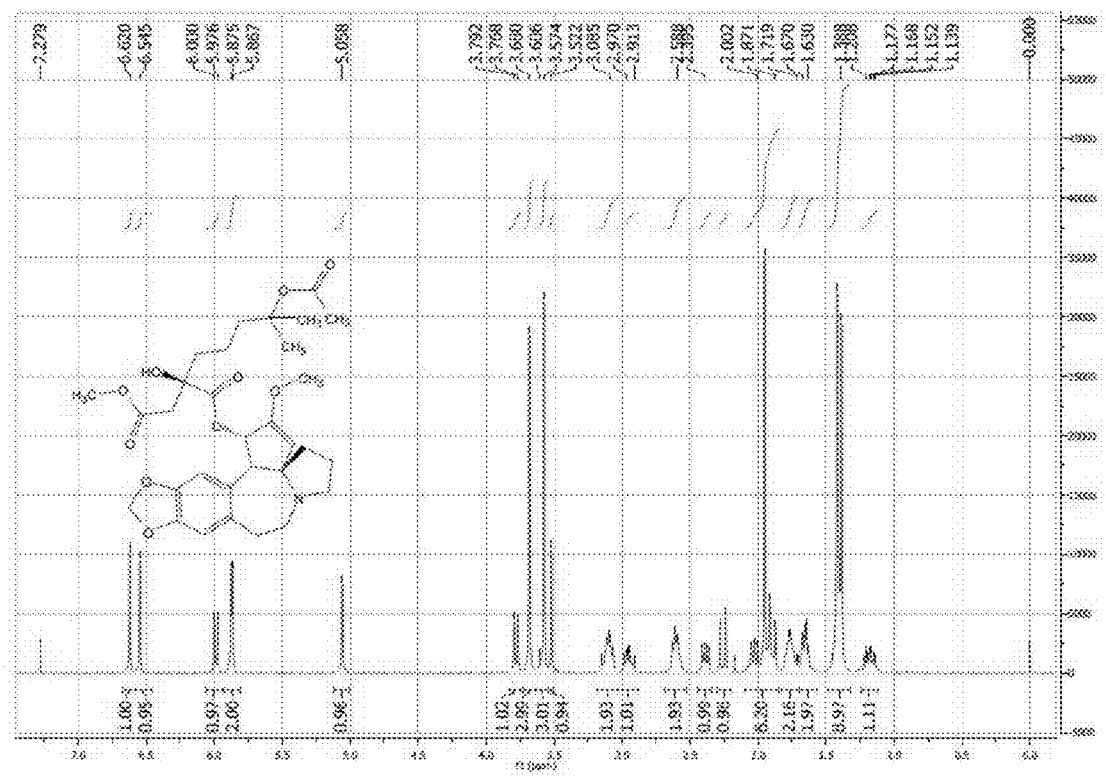
FIG. 1 is a $^1H$ NMR spectrum of compound BS-HH-002.

Specifically, the present invention relates to the following items in particular.

1. A novel mono-acylated homoharringtonine derivative of formula (I) or a novel di-acylated homoharringtonine derivative of formula (II)

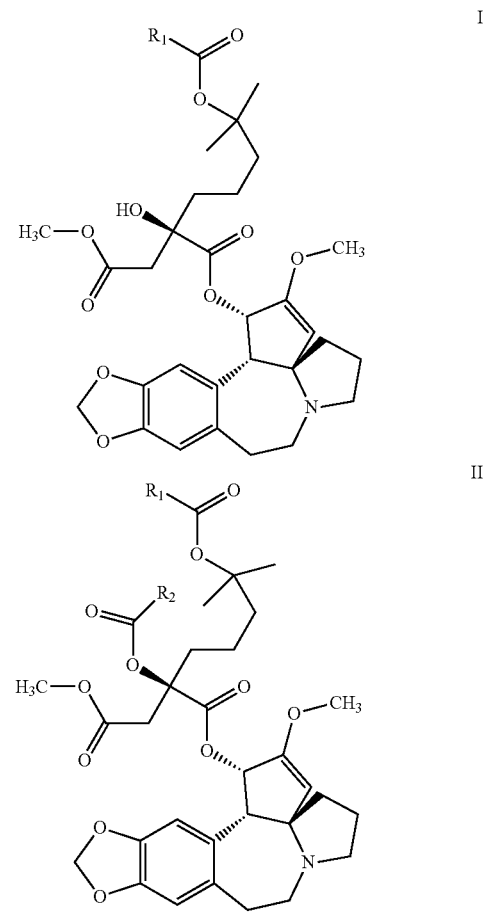

wherein $R_1$ and $R_2$ are independently selected from H, $C_1$-$C_{20}$ alkyl, $C_2$-$C_{20}$ alkenyl, $C_4$-$C_{20}$ conjugated alkenyl, $C_3$-$C_7$ cycloalkyl or cycloalkenyl, aryl, heterocyclyl, heteroaryl, and amino acid side chain residues, which, except for hydrogen, are optionally substituted with one or more substituent selected from the group consisting of halogen, amino, $C_1$-$C_6$ alkylamino, nitro, cyano, hydroxyl, $C_1$-$C_6$ alkoxy, thiol and $C_1$-$C_6$ alkylthio; said $C_3$-$C_7$ cycloalkyl or cycloalkenyl, aryl, heterocyclyl or heteroaryl are optionally substituted with $C_1$-$C_6$ alkyl; and said $C_1$-$C_{20}$ alkyl, $C_2$-$C_{20}$ alkenyl or $C_4$-$C_{20}$ conjugated alkenyl are optionally substituted with aryl or heteroaryl;
or a pharmaceutically acceptable adduct, complex or salt thereof.

2. The acylated homoharringtonine derivative or a pharmaceutically acceptable salt thereof according to item 1, wherein $R_1$ and $R_2$ are independently selected from H, $C_1$-$C_6$ alkyl, $C_2$-$C_6$ alkenyl, $C_4$-$C_8$ conjugated alkenyl, $C_3$-$C_7$ cycloalkyl or cycloalkenyl, aryl, heterocyclic radicals, heteroaryl and amino acid side chain residues, which, except for H, are optionally substituted with one or more substituents selected from the group consisting of halogen, amino, $C_1$-$C_4$ alkyl amino, nitro, cyano, hydroxyl, $C_1$-$C_4$ alkoxy, thiol and $C_1$-$C_4$ alkylthio; said $C_3$-$C_7$ cycloalkyl or cycloalkenyl, aryl, heterocyclic radicals or heteroaryl are optionally substituted with $C_1$-$C_4$ alkyl; and said $C_1$-$C_6$ alkyl, $C_2$-$C_6$ alkenyl or $C_4$-$C_8$ conjugated alkenyl are optionally substituted with aryl or heteroaryl.

3. The acylated homoharringtonine derivative or a pharmaceutically acceptable salt thereof according to item 1, wherein $R_1$ and $R_2$ are independently selected from $C_1$-$C_6$ alkyl, $C_2$-$C_6$ alkenyl, $C_3$-$C_7$ cycloalkyl, aryl and heteroaryl, which are optionally substituted with one or more substituents selected from the group consisting of halogen, amino, $C_1$-$C_4$ alkylamino, nitro, cyano, hydroxyl, $C_1$-$C_4$ alkoxy, thiol and $C_1$-$C_4$ alkylthio; said $C_3$-$C_7$ cycloalkyl, aryl and heteroaryl are optionally substituted with $C_1$-$C_4$ alkyl; and said $C_1$-$C_6$ alkyl or $C_2$-$C_6$ alkenyl are optionally substituted with aryl or heteroaryl.

4. The acylated homoharringtonine derivative or a pharmaceutically acceptable salt thereof according to item 1, wherein $R_1$ and $R_2$ are independently selected from the group consisting of $C_1$-$C_6$ alkyl, a $C_1$-$C_6$ alkyl substituted with aryl or heteroaryl, $C_2$-$C_6$ alkenyl, a $C_2$-$C_6$ alkenyl substituted with aryl or heteroaryl, $C_3$-$C_7$ cycloalkyl, aryl, an aryl substituted with $C_1$-$C_4$ alkyl, heteroaryl and a heteroaryl substituted with $C_1$-$C_4$ alkyl, which are optionally substituted with one or more substituents selected from the group consisting of halogen, amino, $C_1$-$C_4$ alkylamino, nitro, cyano, hydroxyl, $C_1$-$C_4$ alkoxy, thiol and $C_1$-$C_4$ alkylthio.

5. The acylated homoharringtonine derivative or a pharmaceutically acceptable salt thereof according to item 1, wherein $R_1$ and $R_2$ are independently selected from the group consisting of a $C_1$-$C_6$ alkyl, a $C_1$-$C_6$ alkyl substituted with aryl or heteroaryl, a $C_2$-$C_6$ alkenyl, a $C_2$-$C_6$ alkenyl substituted with aryl or heteroaryl, a $C_3$-$C_7$ cycloalkyl, aryl, an aryl substituted with $C_1$-$C_4$ alkyl, a heteroaryl and a heteroaryl substituted with $C_1$-$C_4$ alkyl, each of which is optionally substituted with one or more halogen atoms.

6. The acylated homoharringtonine derivative or a pharmaceutically acceptable salt thereof according to any one of item s 1-5, wherein said aryl is phenyl; said heteroaryl is furanyl, thiophenyl, pyridinyl, oxazolyl or isoxazolyl; said $C_3$-$C_7$ cycloalkyl is cyclopropyl, cyclobutyl, cyclopentyl or cyclohexyl; each of said groups is optionally substituted with $C_1$-$C_4$ alkyl (preferably methyl) or halogen atoms (preferably chlorine or bromine).

7. The acylated homoharringtonine derivative or a pharmaceutically acceptable salt thereof according to any one of item s 1-6, which is a compound of formula (I) or a pharmaceutically acceptable salt thereof.

8. The acylated homoharringtonine derivative or a pharmaceutically acceptable salt thereof according to item 7, wherein $R_1$ is selected from the group consisting of a $C_1$-$C_6$ alkyl, a $C_1$-$C_6$ alkyl substituted with aryl or heteroaryl, a $C_3$-$C_7$ cycloalkyl, an aryl, an aryl substituted with $C_1$-$C_4$ alkyl, a heteroaryl and a heteroaryl substituted with $C_1$-$C_4$ alkyl, each of which is optionally substituted with one or more halogen atoms.

9. The acylated homoharringtonine derivative or a pharmaceutically acceptable salt thereof according to item 8, wherein said aryl is phenyl; said heteroaryl is furanyl, pyridinyl or thiazolyl; said cycloalkyl is cyclopentyl, each of which is optionally substituted with one or more halogen atoms.

10. The acylated homoharringtonine derivative or a pharmaceutically acceptable salt thereof according to item 9, wherein $R_1$ is selected from the group consisting of methyl; furanyl; pyridinyl optionally substituted with halogen; thiazolyl optionally substituted with methyl; phenyl; and cyclopentyl.

Some examples of the compounds of the present invention are shown as follows. The compounds listed are for illustrating the present invention only, and should not be understood as limiting the scope of the present invention in any sense.

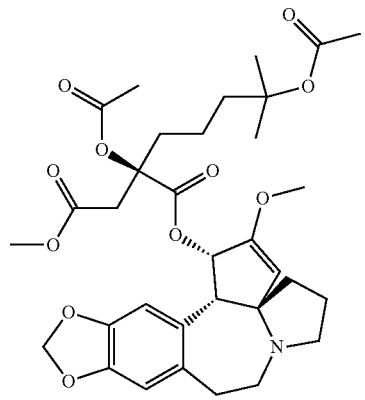

BS-HH-001

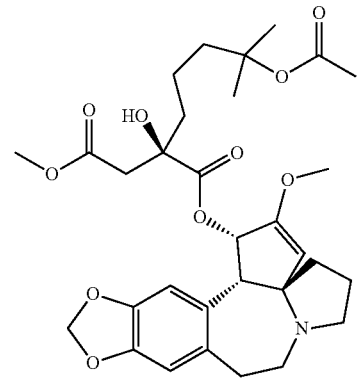

BS-HH-002

-continued

BS-HH-0022

BS-HH-0572

BS-HH-059

BS-HH-061

BS-HH-062

BS-HH-066

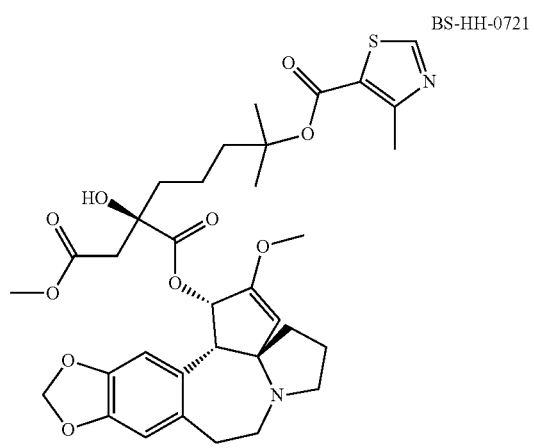
BS-HH-0721
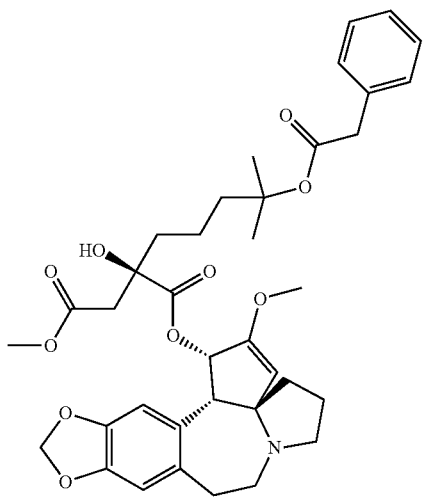
BS-HH-074
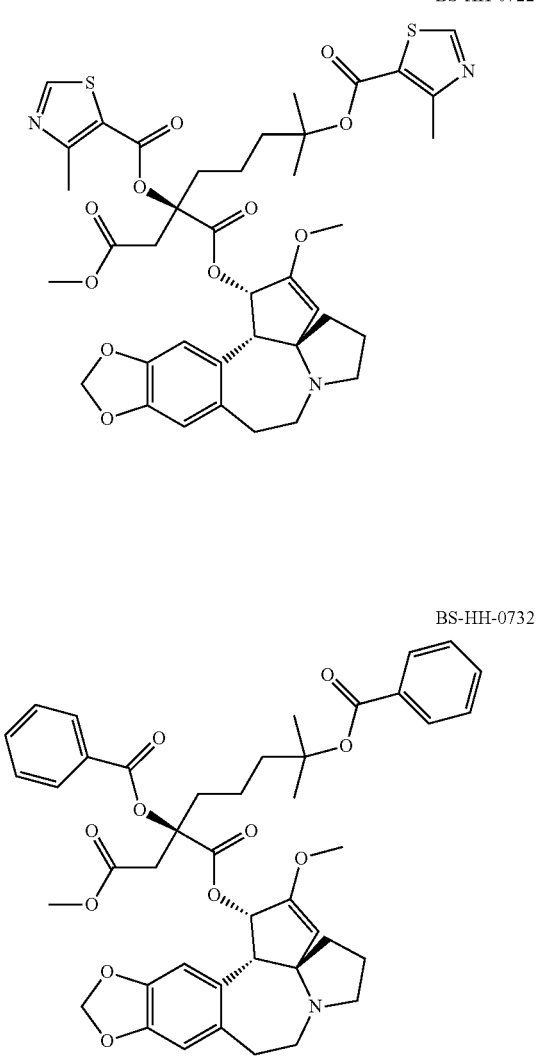
BS-HH-0722
BS-HH-0732
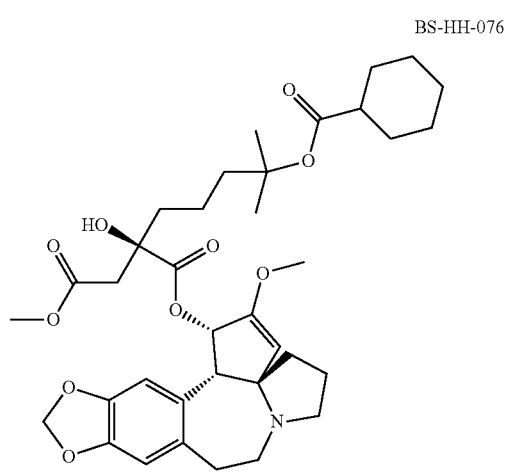
BS-HH-076
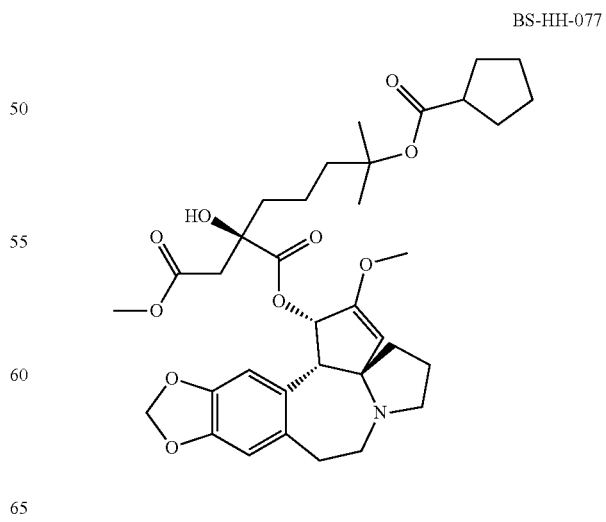
BS-HH-077
Some characterizing data for the compounds shown above are listed in the following table:

| Compound No. | Formula | Molecular Weight | Appearance | State | Yield (%) |
|---|---|---|---|---|---|
| BS-HH-001 | $C_{33}H_{43}NO_{11}$ | 629.7 | White | Solid | 25 |
| BS-HH-002 | $C_{31}H_{41}NO_{10}$ | 587.7 | White | Solid | 66 |
| BS-HH-0022 | $C_{43}H_{47}NO_{13}$ | 785.8 | Light yellow | Powder | 67 |
| BS-HH-0572 | $C_{39}H_{43}NO_{11}S_2$ | 765.9 | Light yellow | Oil | 25 |
| BS-HH-059 | $C_{34}H_{41}NO_{11}$ | 639.7 | Light yellow | Viscous | 18 |
| BS-HH-061 | $C_{34}H_{42}N_2O_{11}$ | 654.7 | White | Solid | 6 |
| BS-HH-062 | $C_{33}H_{43}NO_{10}$ | 613.7 | White | Solid | 18 |
| BS-HH-066 | $C_{35}H_{41}ClN_2O_{10}$ | 685.2 | Red | Viscous | 99 |
| BS-HH-0721 | $C_{34}H_{42}N_2O_{10}S$ | 670.8 | Light yellow | Powder | 12 |
| BS-HH-0722 | $C_{39}H_{45}N_3O_{11}S_2$ | 795.9 | White | Powder | 22 |
| BS-HH-0732 | $C_{43}H_{47}NO_{11}$ | 753.8 | Light yellow | Powder | 65 |
| BS-HH-074 | $C_{37}H_{45}NO_{10}$ | 663.8 | White | Powder | 15 |
| BS-HH-076 | $C_{36}H_{49}NO_{10}$ | 655.8 | Light yellow | Powder | 8 |
| BS-HH-077 | $C_{35}H_{47}NO_{10}$ | 641.7 | Light yellow | Solid | 28 |

The following compounds are particularly preferred according to the present invention:

Compound BS-HH-001

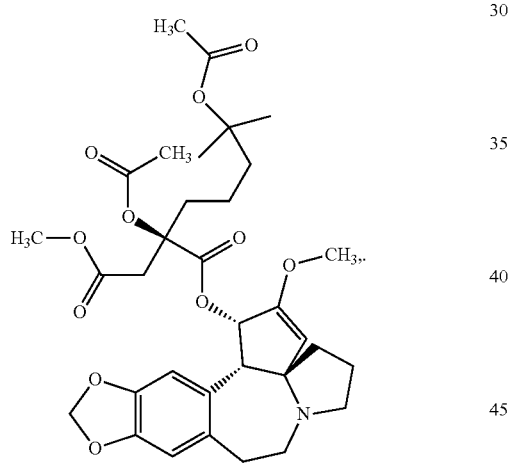

2,6-diacetylhomoharringtonine

Compound BS-HH-002

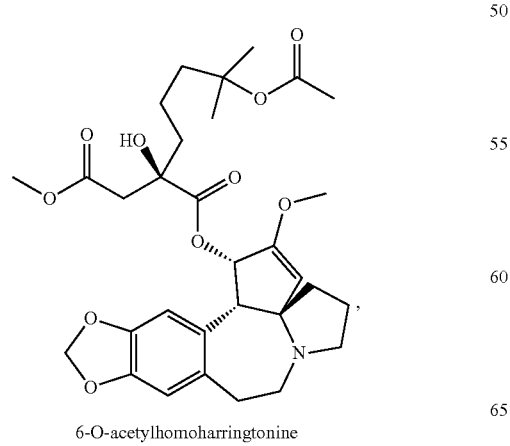

6-O-acetylhomoharringtonine

Compound BS-HH-059

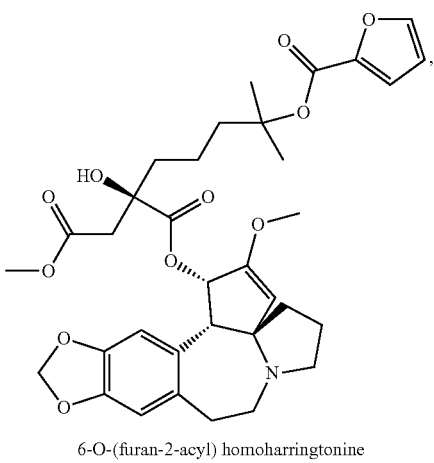

6-O-(furan-2-acyl) homoharringtonine

Compound BS-HH-066

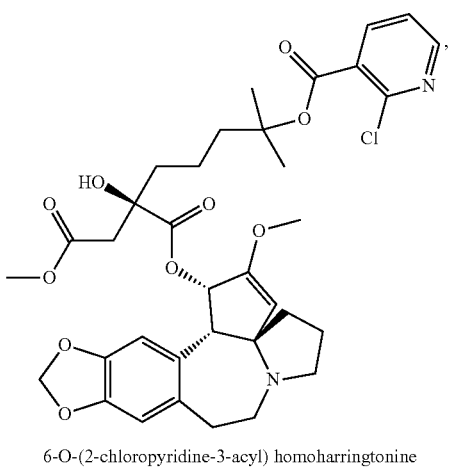

6-O-(2-chloropyridine-3-acyl) homoharringtonine

Compound BS-HH-0721

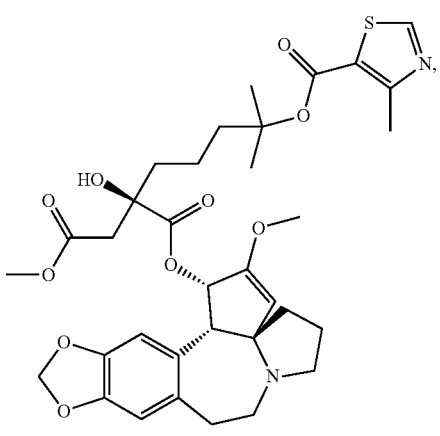

6-O-(4-methylthiazole-5-acyl) homoharringtonine

-continued

Compound BS-HH-074

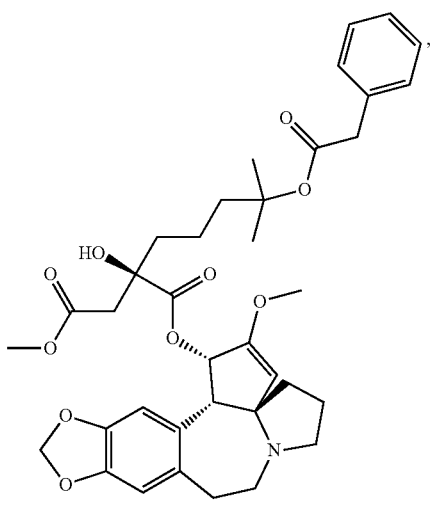

6-O-(phenylacetyl) homoharringtonine

Compound BS-HH-077

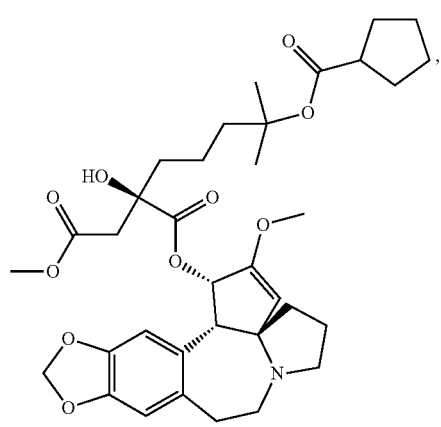

6-O-(cyclovaleryl) homoharringtonine

The present invention also relates to salts, solvates, hydrates, adducts, complexes, polymorphs or prodrugs of the inventive compounds of formula (I) or formula (II).

As used herein, the term "alkyl" refers to a straight or branched hydrocarbon radical containing designated number of carbon atoms, such as $C_1$-$C_{20}$ alkyl, $C_1$-$C_6$ alkyl, $C_1$-$C_4$ alkyl, $C_1$-$C_3$ alkyl, etc. Examples of alkyl include, but not limited to, methyl, ethyl, n-propyl, isopropyl, tert-butyl, n-pentyl, n-hexyl, n-eicosyl, etc.

The term "alkenyl" refers to a straight or branched hydrocarbon radical containing designated number of carbon atoms and at least one carbon-carbon double bond, such as $C_2$-$C_{20}$ alkenyl, $C_2$-$C_{10}$ alkenyl, $C_2$-$C_8$ alkenyl, $C_2$-$C_7$ alkenyl, $C_2$-$C_6$ alkenyl, $C_2$-$C_4$ alkenyl, $C_2$-$C_3$ alkenyl, etc. Examples of alkenyl include, but not limited to, vinyl, allyl and eicosenyl.

The term "conjugated alkenyl" refers to a straight or branched hydrocarbon radical containing designated number of carbon atoms and at least two carbon-carbon double bonds that are conjugated, such as $C_4$-$C_{20}$ conjugated alkenyl, $C_4$-$C_{18}$ conjugated alkenyl, $C_4$-$C_{10}$ conjugated alkenyl, $C_4$-$C_8$ conjugated alkenyl, $C_4$-$C_7$ conjugated alkenyl, $C_4$-$C_6$ conjugated alkenyl, $C_4$-$C_5$ conjugated alkenyl, etc. Examples of conjugated alkenyl include, but not limited to, conjugated butadienyl, and (9Z)-octadec-9-enyl.

The term "$C_3$-$C_7$ cycloalkyl or cycloalkenyl" refers to a saturated or unsaturated 3-7 membered monocyclic hydrocarbon radical. Representative examples of $C_3$-$C_7$ cycloalkyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 carbon atoms. In the case of polycyclic aryl, at least one ring is aromatic. Aryl can also be one fused with a heterocyclic radical. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

"Heterocyclyl" refers to a non-aromatic cyclic group containing 1-4 heteroatoms (e.g. 1, 2, 3 or 4 heteroatoms) as ring atoms. A heteroatom refers to nitrogen, oxygen or sulfur. A heterocyclic radical can be a monocyclic heterocyclic radical having 4-8 ring atoms or a bicyclic heterocyclic radical having 7-11 ring atoms. A heterocyclic radical can be saturated, or can be unsaturated and meanwhile non-aromatic. Examples of heterocyclic radicals include azacyclobutyl, pyrrolidinyl, tetrahydrofuranyl, dihydrofuranyl, piperazinyl, piperidinyl, tetrahydropyranyl, tetrahydrothiophenyl, etc.

The term "amino acid" refers to natural amino acids.

The term "amino acid side chain residue" refers to the amino acid moiety other than carboxyl on the α-carbon.

The term "halogen" refers to fluorine, chlorine, bromine or iodine.

The term "alkylamino" refers to an amino group substituted with one or two alkyl (including cycloalkyl) having designated number of carbon atoms.

The term "alkoxy" includes alkoxy and cycloalkyloxy.

The term "alkylthio" includes alkylthio and cycloalkylthio.

The term "pharmaceutically acceptable adducts, or complexes of the compounds of formula (I) or formula (II)" refers to the product formed by a compound of the present invention with further combined small molecule or biological macromolecule via a non-chemical bond or non-covalent intermolecular force.

As used herein, the term "pharmaceutically acceptable salts of the compounds of formula (I) or formula (II)" refers to the organic acid salts formed by the compounds of the present invention with an organic acid which comprises a pharmaceutically acceptable anion. These organic acid salts include, but not limited to, tosylate, methanesulfonate, malate, acetate, citrate, malonate, tartrate, succinate, benzoate, ascorbate, lactate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate and the like.

A pharmaceutically acceptable salt may be obtained using standard procedures well known in the art, for example by reacting a sufficient amount of alkaline compound with a suitable acid that provides a pharmaceutically acceptable anion.

As used herein, the term "polymorph" means a solid crystalline form of the compound of the present invention or a complex thereof. Various polymorphs of one same compound may exhibit different physical, chemical and/or spectroscopic properties. The different physical properties include, but not limited to, stability (e.g., thermal or light stability), compressibility and density (which are important for formulation and manufacture of the product), and dissolution rate (which may affect its bioavailability and absorbability). Differences in stability may result in a change in chemical reactivity (e.g., differential oxidation, such that a dosage form comprised of one polymorph discolors more rapidly than one comprised of another polymorph) or mechanical properties (e.g., in storage, crushed parts of the tablet of a kinetically favored polymorph is converted to a thermodynamically more stable polymorph) or both (e.g., tablets composed of one polymorph are more susceptible to breakdown at high humidity). Different physical properties of various polymorphs may affect their processing. For example, one polymorph may be more likely to form a solvate or may be more difficult to be filtered out or purified by washing than another one due to, for example, their different particle shapes or size distributions.

As used herein, the term "hydrate" means such a compound of the present invention or a salt thereof as further comprising a stoichiometric or non-stoichiometric amount of water bound via non-covalent intermolecular forces.

Unless otherwise indicated, the term "prodrug" used herein means a derivative of an inventive compound that, via hydrolyzation, oxidization, or other reactions under a biological condition (in vitro or in vivo), can provide a compound of this invention. A prodrug may only become active upon such a reaction under a biological condition, or may have activities in its unreacted form. Typically, a prodrug can be prepared using known methods, such as those described in *Burger's Medicinal Chemistry and Drug Discovery* (1995) 172-178, 949-982 (Manfred E. Wolff, 5th edition), *Prodrugs and Targeted Delivery* by J. Rautio (2011) 31-60 (Wiley-VCH, *Methods and Principles in Medicinal Chemistry*, Vol. 47), and *Fundamentals of Medicinal Chemistry* (2003) by G. Thomas, 195-200 (Wiley).

In the compounds of the present invention, the homoharringtonine derivatives have four chiral centers in the stereochemical structure represented by the structural formula I and formula II. The stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate a plane of plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention is typically prepared as follows.

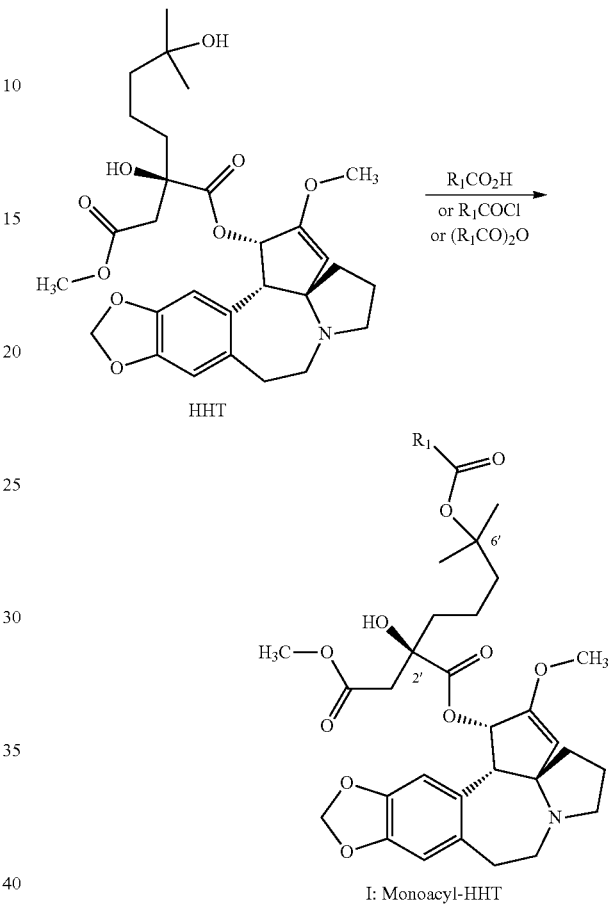

I: Monoacyl-HHT

The compounds of formula (I) which are acylated or esterified at 6-position can be prepared by reacting extracted natural homoharringtonine (HHT) with appropriate organic acids, organic anhydrides or organic acyl chlorides. $R_1$ in formula (I) is as defined above for formula (I).

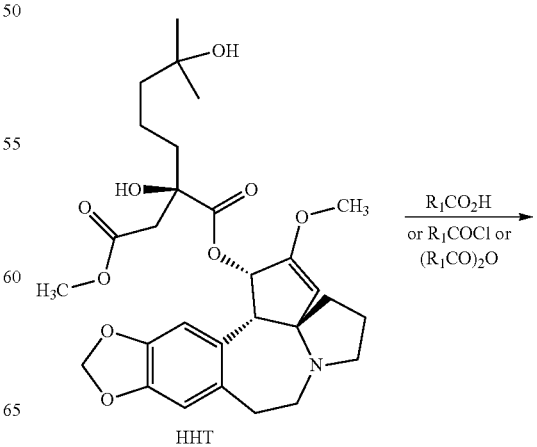

19
-continued

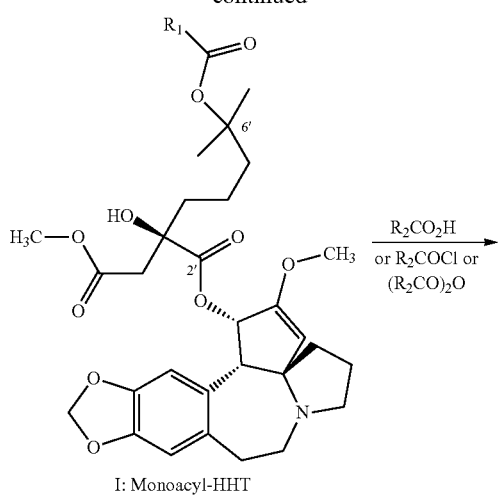

I: Monoacyl-HHT

20
-continued

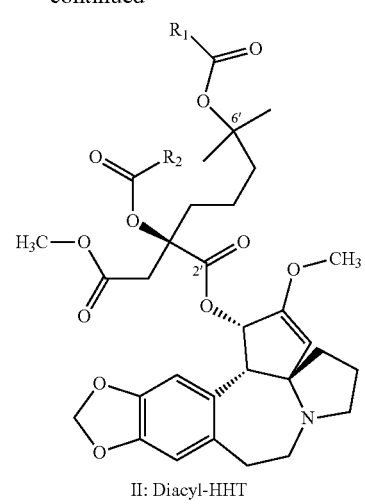

II: Diacyl-HHT

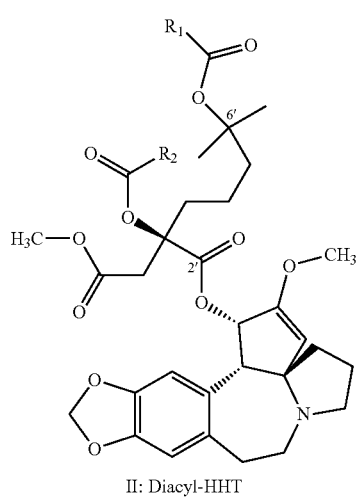

II: Diacyl-HHT

The compound of formula (II) which is diacylated or diesterified at 2'- and 6'-position can also be prepared in a one-step process by reacting extracted natural homoharringtonine (HHT) with appropriate organic acids, organic anhydrides or organic acyl chlorides. Alternatively, they can also be prepared in a two-step process by reacting an intermediate of formula (I) compounds with appropriate organic acids, organic anhydrides or organic acyl chlorides. $R_1$ and $R_2$ in formula (II) are defined as above for formula (II).

For example, the present invention provides the following process for preparing the mono-acylated homoharringtonine derivatives of formula (I) of the present invention:

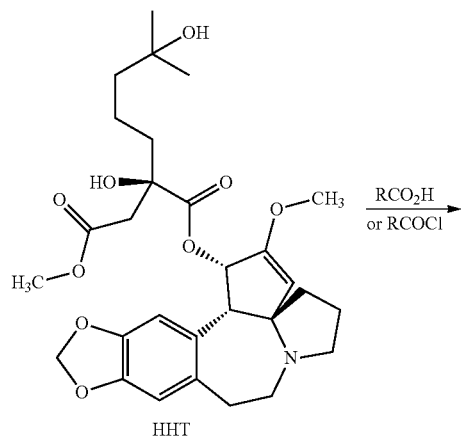

HHT

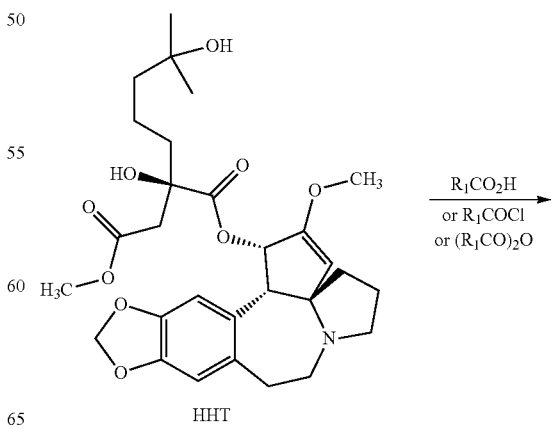

HHT

-continued

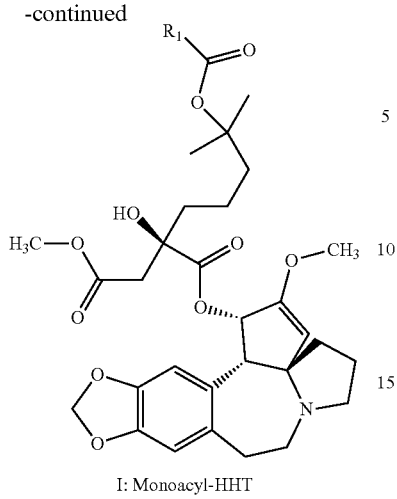

I: Monoacyl-HHT

-continued

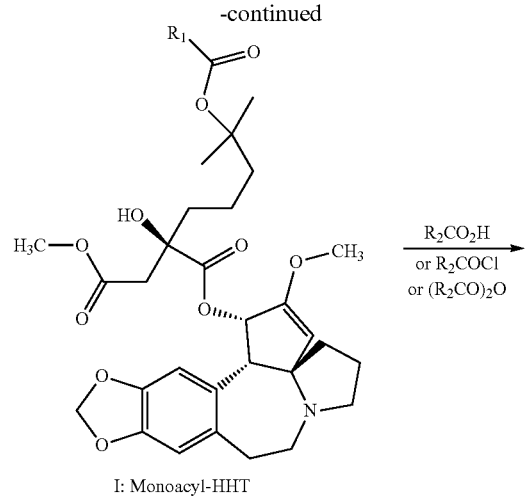

I: Monoacyl-HHT

A mono-acylated homoharringtonine derivative of formula (I) can be prepared by subjecting homoharringtonine and an organic acid $R_1CO_2H$ to condensation esterification in the presence of a condensing agent or a catalyst. It can also be prepared by subjecting homoharringtonine and an organic acyl chloride $R_1COCl$ or organic anhydride $(R_1CO)_2O$ to condensation esterification in the presence of a condensing agent or a alkaline reagent. A mono-acylated homoharringtonine alkaline derivative of formula (I) can be prepared by activating an organic acid $R_1CO_2H$ into an intermediate, which subsequently reacts with homoharringtonine. A mono-acylated homoharringtonine alkaline derivative of formula (I) can also be prepared by activating the hydroxyl of homoharringtonine to form an intermediate, which subsequently reacts with an organic acid $R_1CO_2H$. The definition of $R_1$ in formula (I), $R_1$ in the organic acid $R_1CO_2H$ and $R_1$ in the organic acyl chloride $R_1COCl$ are identical to those defined in formula (I) above.

The present invention also provides the following process for preparing the di-acylated homoharringtonine derivatives of formula (II) of the present invention:

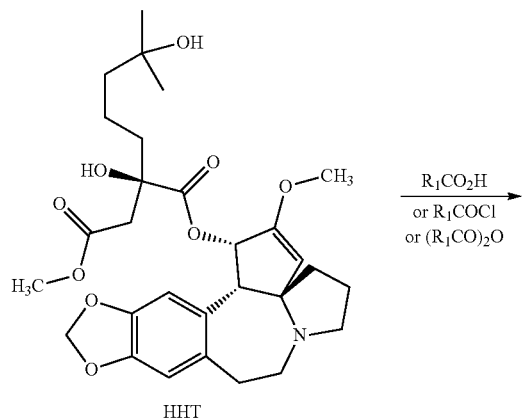

HHT

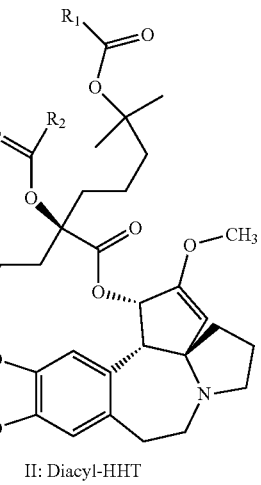

II: Diacyl-HHT

A di-acylated homoharringtonine derivative of formula (II) can be prepared by firstly producing the mono-acylated homoharringtonine derivative of formula (I) according to the above process, and subsequently subjecting said derivative of formula (I) and an organic acid $R_2CO_2H$ to condensation esterification in the presence of a condensing agent or a catalyst. It can also be prepared by subjecting said mono-acylated homoharringtonine derivative of formula (I) and an organic acyl chloride $R_2COCl$ or organic anhydride $(R_2CO)_2O$ to condensation esterification in the presence of a condensing agent or a alkaline reagent. A di-acylated homoharringtonine alkaline derivative of formula (II) can be prepared by activating an organic acid $R_2CO_2H$ into an intermediate, which reacts subsequently with the mono-acylated homoharringtonine alkaline derivative of formula (I). A di-acylated homoharringtonine alkaline derivative of formula (II) can also be prepared by activating the hydroxyl of the mono-acylated homoharringtonine alkaline derivative of formula (I) to form an intermediate, which reacts subsequently with an organic acid $R_2CO_2H$.

$R_1$ in formula (I), $R_1$ in the organic acid $R_1CO_2H$, $R_1$ in the organic acyl chloride $R_1COCl$ and $R_1$ in the organic anhydride $(R_1CO)_2$ are all identical to those defined in formula (I) above. $R_1$ and $R_2$ in formula (II), $R_1$ in the organic acid $R_1CO_2H$, $R_1$ in the organic acyl chloride $R_1COCl$, $R_2$ in the organic acid $R_2CO_2H$ and $R_2$ in the organic acyl chloride $R_2COCl$ are all identical to those defined in formula (I) and in formula (II) above. The above process is more suitable for preparing those derivatives in which $R_1$ and $R_2$ are different. For those di-acylated derivatives in which $R_1$ and $R_2$ are the same, the preparation thereof can be conducted according to the following process.

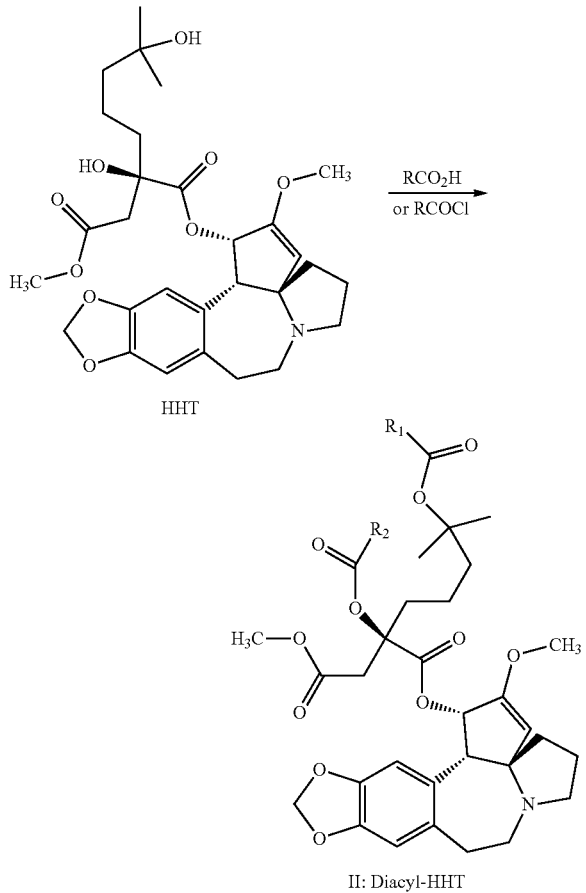

The said di-acylated homoharringtonine derivative of formula (II) can be prepared by increasing the molar ratio of the organic acid feed, elongating the reaction duration, and/or employing stronger activating reagents. The above organic acid $RCO_2H$ can be the organic acid $R_1CO_2H$ or the organic acid $R_2CO_2H$; $R_1$ and $R_2$ in formula (II) are identical to those defined in formula (II) above.

The above reaction is typically carried out in the presence of an alkali or an alkaline reagent. The alkali herein can be, but not limited to, an organic alkali, such as diisopropylethylamine, triethylamine, or dimethylaminopyridine.

The above reaction typically is carried out in a solution. The solvents used herein include, but not limited to, aprotic polar solvents, such as dichloromethane (DCM), dimethylsulfoxide (DMSO), dimethylformamide (DMF) or tetrahydrofuran (THF) etc.

The above reaction typically takes place at a temperature of 0° C.-50° C., which generally varies with the raw material and the alkali used.

The raw material for the preparation reaction is homoharringtonine (HHT), which is obtained by extraction from natural products and is commercially available.

The organic acids, organic anhydrides or organic acyl chlorides for the preparation reaction are commercially available.

Conventional chemical conversion processes may be used to practice this invention. One skilled person in the art can determine suitable chemical agents, solvents, protecting groups, and reaction conditions for these chemical conversions. Relevant information are described, for example, in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) or formula (II) of the present invention.

The present invention provides a pharmaceutical composition which comprises at least one compound of formula (I) or formula (II) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally or parenterally (for example, by an intravenous, intramuscular, topical or subcutaneous route).

Thus, the present compounds may be systemically administered, e.g., orally administered, in conjugation with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or in a device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredient (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The homoharringtonine derivative of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be obtained by a synthesis method known in the art.

Example 1

Synthesis of Compound BS-HH-001

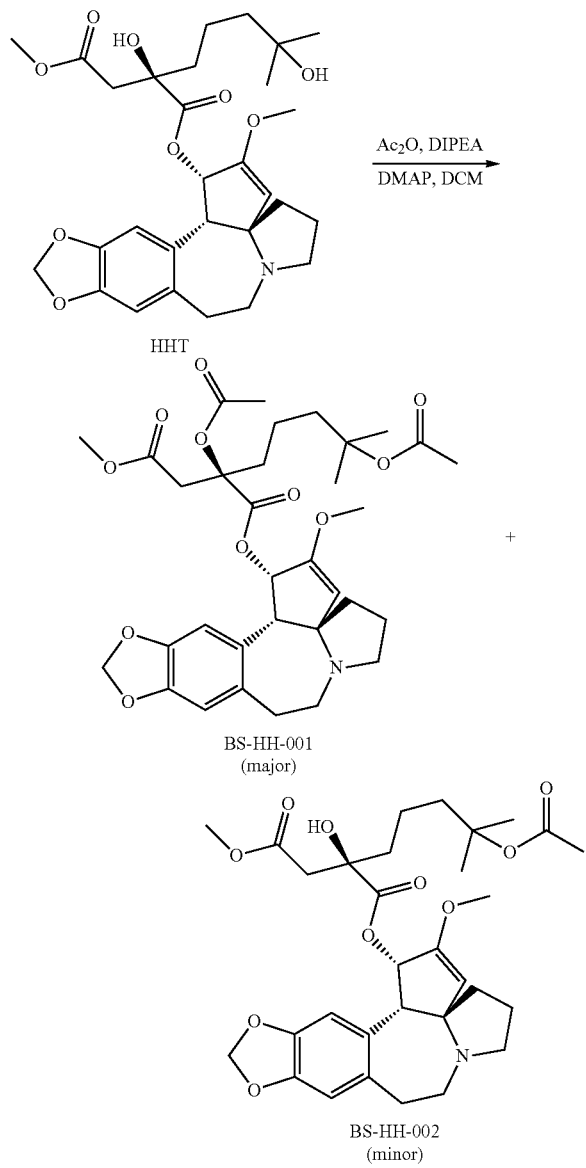

BS-HH-001 (major)

BS-HH-002 (minor)

wherein, HHT: homoharringtonine; Ac$_2$O: acetic anhydride; DIPEA: N,N-diisopropylethylamine; DMAP: 4-dimethylaminopyridine; DCM: dichloromethane; BS-HH-001: 2,6-diacetylhomoharringtonine; BS-HH-002: 6-acetylhomoharringtonine.

Homoharringtonine HHT (125 mg, 0.23 mmol), N,N-diisopropylethylamine (444 mg, 3.44 mmol) and 4-dimethylaminopyridine (28 mg, 0.023 mmol) are dissolved in dichloromethane (2 mL). Acetic anhydride (351 mg, 3.44 mmol) is added to the mixed solution and reacted for 24 h under 35° C. The reaction solution is rinsed with water and then with saturated sodium bicarbonate, dried and concentrated. The resulted crude product is purified via Preparative Liquid Chromatography to give compound BS-HH-001 (43.3 mg, 30%) as a white solid.

LC-MS: retention time: 1.11 min (98.7%), m/z: 630.5 [M+H]$^+$.

$^1$H NMR (300 MHz, CDCl$_3$): δ 6.60 (d, 2H), 5.80-5.93 (m, 3H), 5.02 (s, 1H), 3.76 (d, J=9.9 Hz, 1H), 3.67 (s, 3H), 3.60 (s, 3H), 3.03-3.17 (m, 2H), 2.84 (d, J=15.0 Hz, 1H), 2.52-2.67 (m, 3H), 2.37 (dd, J=13.5 Hz, 6.3 Hz, 1H), 2.00 (s, 3H), 1.95 (s, 3H), 1.39 (d, 6H).

Example 2

Synthesis of Compound BS-HH-002

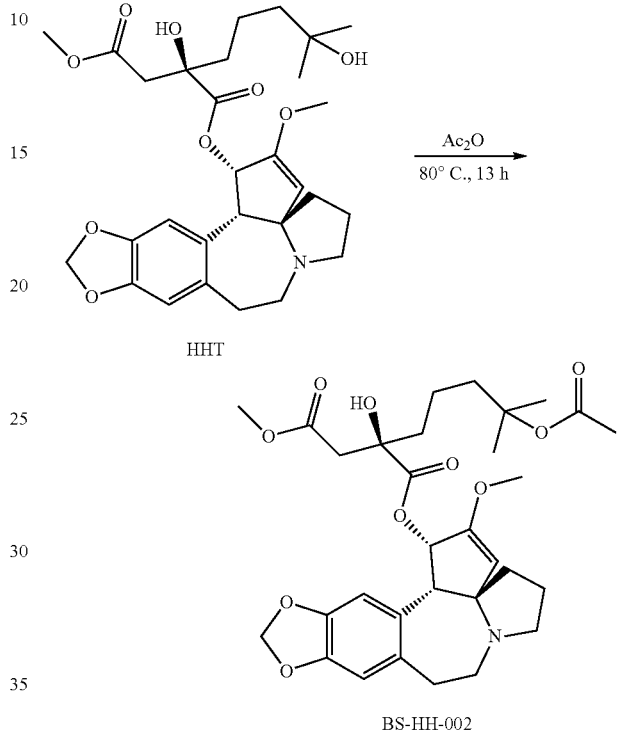

BS-HH-002 wherein, HHT: homoharringtonine; Ac$_2$O: acetic anhydride.

Homoharringtonine HHT (1 g, 1.84 mmol) is added to Ac$_2$O (20 mL) and the reaction mixture is heated up to 80° C. and stirred for 13 h. After the reaction is completed, the reaction solution is concentrated to give a viscous crude product, to which diethyl ether is added for curing. Ethyl acetate is then added to the cured crude product to dissolve it. The mixture is rinsed with a saturated solution of potassium carbonate and then concentrated. The resulted crude product is purified by a Silica Gel Column Chromatography (EA:PE=1:2) to give a yellow oil, which is then recrystallized with diethyl ether to give compound BS-HH-002 (654 mg, 61%) as a white solid; the homoharringtonine HHT raw material is recovered in the meantime (354 mg).

BS-HH-002: LC-MS: retention time: 1.00 min (96.74%), m/z: 588.2 [M+H]$^+$.

$^1$H NMR (400 MHz, CDCl$_3$): δ 6.62 (s, 1H), 6.55 (s, 1H), 5.99 (d, J=9.6 Hz, 1H), 5.87 (d, J=3.2 Hz, 2H), 5.06 (s, 1H), 3.78 (d, J=9.6 Hz, 1H), 3.68 (s, 3H), 3.57 (s, 3H), 3.52 (s, 1H), 3.15-3.07 (m, 2H), 2.99-2.91 (m, 1H), 2.63-2.59 (m, 2H), 2.41-2.36 (m, 1H), 2.21 (d, J=16.4 Hz, 1H), 2.05-1.87 (m, 6H), 1.76 (m, 2H), 1.68-1.63 (m, 2H), 1.46-1.39 (m, 9H), 1.23-1.14 (m, 1H). $^{13}$C NMR (400 MHz, CDCl$_3$): δ 173.91, 170.41, 170.30, 157.65, 146.62, 145.75, 133.11, 128.13, 112.60, 109.57, 100.75, 100.03, 82.14, 74.67, 74.41, 70.57, 57.31, 55.63, 53.81, 51.47, 48.48, 43.17, 42.36, 40.57, 38.76, 31.14, 25.70, 22.44, 20.44, 20.13, 17.44.

Figure 2:
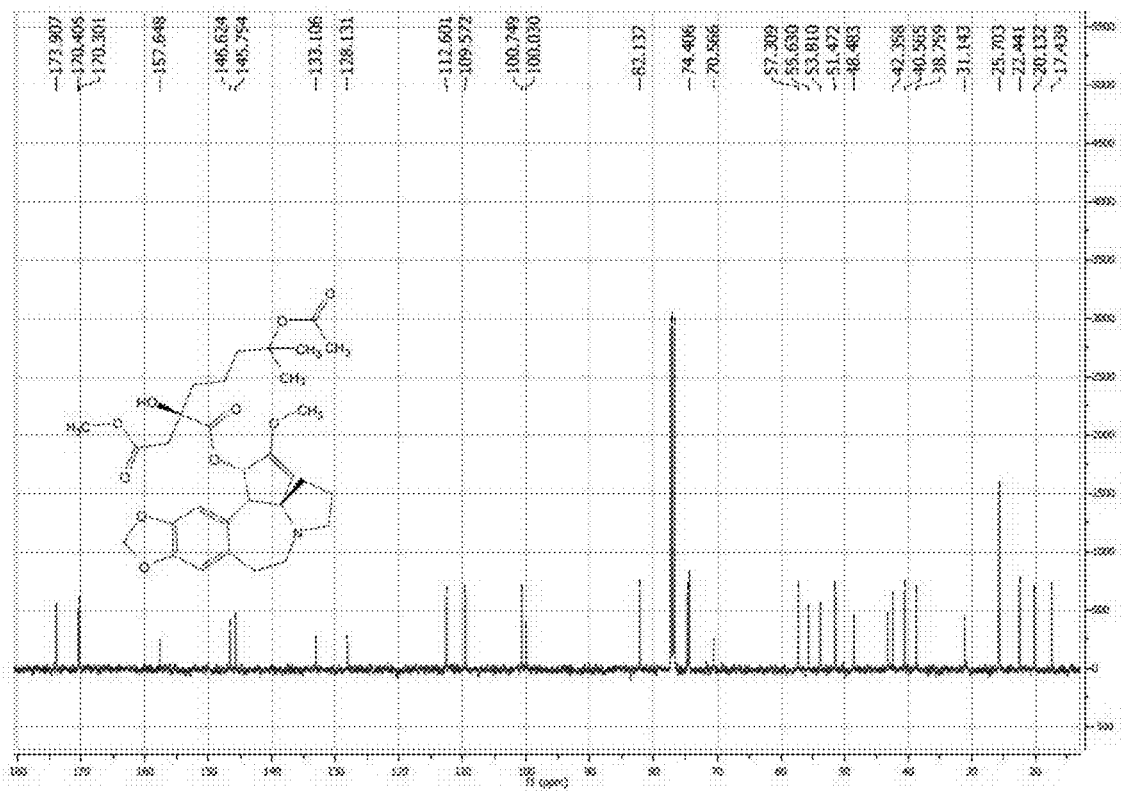
FIG. 2 is a $^{13}C$ NMR spectrum of compound BS-HH-002.
Figure 3:
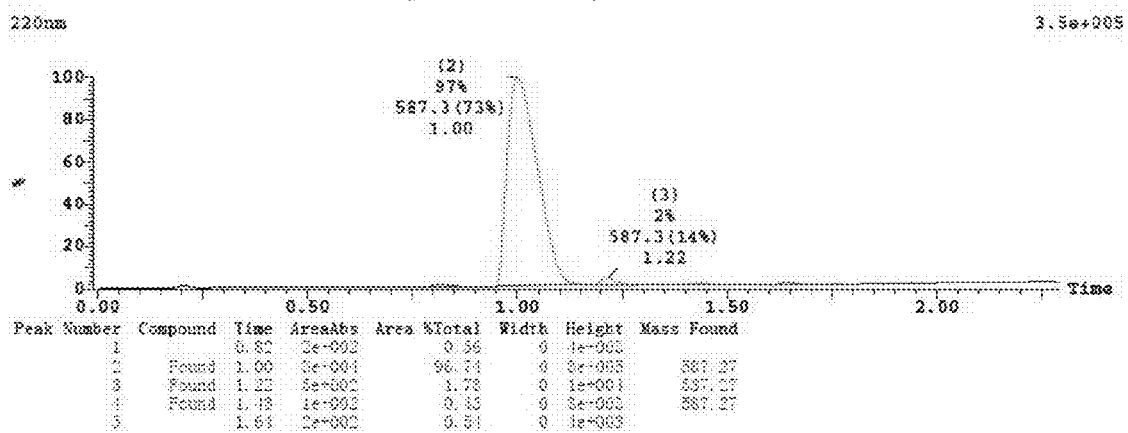
FIG. 3 is a LC-MS spectrum of compound BS-HH-002.

$^1$H NMR spectrum of the resulted compound BS-HH-002 is shown in FIG. 1, $^{13}$C NMR spectrum in FIG. 2 and LC-MS spectrum in FIG. 3.

Example 3

Synthesis of Compound BS-HH-077

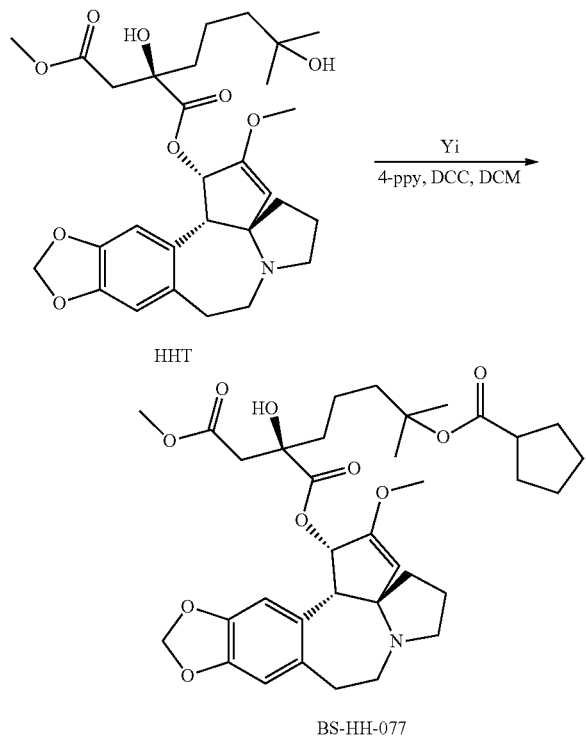

wherein, HHT: homoharringtonine; Yi: cyclopentylformic acid; 4-ppy: 4-(1'-tetrahydropyrrole)pyridine; DCC: dicyclohexylcarbodiimide; DCM: dichloromethane.

Homoharringtonine (110 mg, 0.2 mmol), cyclopentylformic acid (46 mg, 0.4 mmol) and 4-(1'-tetrahydropyrrole)pyridine (60 mg, 0.4 mmol) are dissolved in dichloromethane (2 mL). Dicyclohexylcarbodiimide (83 mg, 0.4 mmol) is added to the solution, which is heated and refluxed for 3 h before filtration. The filtrate is concentrated, and the resulted crude product is purified with High Performance Liquid Chromatography to give BS-HH-077 (35.9 mg, 28%) as a light yellow powdery solid.

LC-MS: retention time: 1.52 min (95.63%), m/z: 642.6 [M+H]$^+$.

$^1$H NMR (300 MHz, CDCl$_3$): δ 6.63 (s, 1H), 6.59 (s, 1H), 5.99 (d, J=9.0 Hz, 1H), 5.90 (m, 2H), 5.09 (s, 1H), 3.80 (m, 1H), 3.73 (s, 3H), 3.57 (s, 3H), 3.49-3.54 (m, 1H), 2.73-3.02 (m, 2H), 2.42-2.65 (m, 3H), 2.27 (m, 1H), 2.03-2.24 (m, 3H), 1.76-1.84 (m, 3H), 1.56 (m, 2H), 1.40 (d, 6H).

BS-HH-0022 is prepared according to the process for BS-HH-001 using the same reagents by reacting homoharringtonine with furan-2-acrylic acid.

LC-MS: retention time: 1.69 min (70.42%), m/z: 786.8 [M+H]$^+$.

$^1$H NMR (300 MHz, CDCl$_3$): δ 7.46 (d, J=6 Hz, 2H), 7.37-7.29 (m, 2H), 6.60 (m, 4H), 6.46 (s, 2H), 6.25 (d, 2H), 5.93 (m, 3H), 3.71 (s, 3H), 3.57 (s, 3H), 1.46 (s, 6H).

BS-HH-0572 is prepared according to the process for BS-HH-001 using the same reagents by reacting homoharringtonine with thiophen-2-carboxylic acid.

LC-MS: retention time: 1.65 min (94.68%), m/z: 766.5 [M+H]$^+$.

$^1$H NMR (300 MHz, CDCl$_3$): δ 7.71 (m, 2H), 7.53 (m, 2H), 7.05 (m, 2H), 6.60 (d, 2H), 5.99 (d, 1H), 3.75 (s, 1H), 3.62 (s, 3H), 3.52 (s, 3H), 2.24 (s, 2H), 1.55 (d, 6H).

BS-HH-059 is prepared according to the process for BS-HH-077 using the same reagents by reacting homoharringtonine with furan-2-carboxylic acid.

LC-MS: retention time: 1.41 min (100%), m/z: 640.3 [M+H]$^+$.

$^1$H NMR (300 MHz, CDCl$_3$): δ 7.54 (m, 1H), 7.05 (d, 1H), 6.58 (s, 1H), 6.53 (s, 1H), 6.47 (m, 1H), 5.99 (d, J=9.0 Hz, 1H), 5.86 (m, 2H), 5.03 (s, 1H), 3.78 (d, J=9.0 Hz, 1H), 3.65 (s, 3H), 3.56 (s, 3H), 3.51 (s, 1H), 3.12 (m, 2H), 2.61 (m, 1H), 2.38 (dd, J=9 Hz, 2H), 1.86 (m, 2H), 1.54 (d, 6H).

BS-HH-061 is prepared according to the process for BS-HH-077 using the same reagents by reacting homoharringtonine with 5-methylisoxazole-4-carboxylic acid.

LC-MS: retention time: 1.46 min (89.16%), m/z: 655.6 [M+H]$^+$.

$^1$H NMR (300 MHz, CDCl$_3$): δ 6.63 (s, 1H), 6.55 (s, 1H), 6.00 (d, J=9.0 Hz, 1H), 5.87 (m, 2H), 5.34 (s, 1H), 5.06 (s, 1H), 3.81 (d, J=12 Hz, 1H), 3.69 (s, 3H), 3.57 (s, 3H), 3.48 (s, 1H), 2.61 (m, 2H), 2.31 (m, 2H), 2.26 (s, 3H), 1.49 (s, 6H).

BS-HH-062 is prepared according to the process for BS-HH-077 using the same reagents by reacting homoharringtonine with cyclopropanecarboxylic acid.

LC-MS: retention time: 1.40 min (93.07%), m/z: 614.6 [M+H]$^+$.

$^1$H NMR (300 MHz, CDCl$_3$): δ 6.62 (s, 1H), 6.57 (s, 1H), 6.02 (d, J=12.0, 1H), 5.90 (m, 2H), 5.05 (s, 1H), 3.71 (m, 4H), 3.57-3.49 (m, 4H), 1.41 (d, 6H), 0.90 (m, 2H), 0.77 (m, 2H).

BS-HH-066 is prepared according to the process for BS-HH-077 using the same reagents by reacting homoharringtonine with 2-chloronicotinic acid.

LC-MS: retention time: 1.41 min (99.12%), m/z: 685.7 [M+H]$^+$.

BS-HH-0721 is prepared according to the process for BS-HH-077 using the same reagents by reacting homoharringtonine with 4-methylthiazole-5-carboxylic acid.

LC-MS: retention time: 1.40 min (91.07%), m/z: 671.6.

$^1$H NMR (300 MHz, CDCl$_3$): δ 8.73 (s, 1H), 6.60 (s, 1H), 6.56 (s, 1H), 6.00 (d, J=9.0 Hz, 1H), 5.89 (m, 2H), 5.15 (s, 1H), 3.76-3.84 (m, 1H), 3.68 (s, 3H), 3.57 (s, 3H), 3.48 (s, 1H), 2.73 (s, 3H), 1.52 (d, 6H).

BS-HH-0722 is prepared according to the process for BS-HH-001 using the same reagents by reacting homoharringtonine with 4-methylthiazole-5-carboxylic acid.

LC-MS: retention time: 1.54 min (92.92%), m/z: 796.9 [M+H]$^+$.

$^1$H NMR (300 MHz, CDCl$_3$): δ 8.74 (d, 2H), 6.64 (d, 2H), 5.93 (m, 3H), 5.05 (s, 1H), 3.78 (m, 1H), 3.67 (s, 3H), 3.54 (s, 3H), 3.48 (s, 3H), 3.10 (m, 2H), 2.73 (d, 6H), 1.54 (d, 6H).

BS-HH-0732 is prepared according to the process for BS-HH-001 using the same reagents by reacting homoharringtonine with benzoic acid.

LC-MS: retention time: 1.69 min (78.92%), m/z: 754.8 [M+H]$^+$.

$^1$H NMR (300 MHz, CDCl$_3$): δ 7.98-7.88 (m, 4H), 7.53 (m, 2H), 7.43-7.36 (m, 4H), 6.66 (s, 1H), 6.60 (s, 1H), 5.93 (m, 3H), 5.92 (m, 3H), 3.63 (s, 3H), 3.49 (s, 3H), 1.55 (d, 6H).

BS-HH-074 is prepared according to the process for BS-HH-077 using the same reagents by reacting homoharringtonine with phenylacetic acid.

LC-MS: retention time: 1.48 min (87.91%), m/z: 664.7 [M+H]$^+$.

$^1$H NMR (300 MHz, CDCl$_3$): δ 7.28-7.34 (m, 5H), 6.62 (s, 1H), 6.58 (s, 1H), 5.99 (d, J=9.0, 1H), 5.9 (m, 2H), 3.69 (s, 1H), 3.58 (s, 3H), 3.50 (s, 3H), 3.48 (s, 1H), 1.40 (s, 3H), 1.37 (s, 3H).

BS-HH-076 is prepared according to the process for BS-HH-077 using the same reagents by reacting homoharringtonine with cyclohexanecarboxylic acid.

LC-MS: retention time: 1.56 min (79.98%), m/z: 656.6 $[M+H]^+$.

$^1$H NMR (300 MHz, CDCl$_3$): δ 6.61 (s, 1H), 6.55 (s, 1H), 5.97 (d, J=9.0, 1H), 5.88 (m, 2H), 5.06 (s, 1H), 3.81 (d, 1H), 3.70 (s, 3H), 3.57 (s, 3H), 3.48 (s, 1H), 1.40 (s, 3H), 1.36 (s, 3H).

Example 9

Evaluation of the Homoharringtonine Derivatives of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection (CCTCC).

Reagents: The standard sample of homoharringtonine (HHT) is purchased from Taihua Natural Plant Pharmaceutical Co., Ltd., Shaanxi, China, the homoharringtonine derivatives of the present invention.

Main apparatuses: a Thermo Scientific 3111 incubator and a Bio-Rad iMark microplate reader.

(2) Experimental Method

Obtaining 6000 well-growing leukemia cells and inoculating them into wells of a 96-well cell culture plate. The culture medium is the 1640 cell culture medium containing 10% fetal bovine serum. After adding the homoharringtonine derivatives of different concentrations and mixing uniformly, placing the plate in a carbon dioxide cell incubator (5% $CO_2$) at 37° C. and incubated for 72 hours. Then the viable cell concentration is determined by the MTT method. In this experiment, the cell viability in control group (not treated with any compound) is set as 100%. On such basis, the cell viability (%) after treatment and the 50% inhibiting concentration of the compound for the leukemia cell growth at 72 hours ($IC_{50}$ value of 72 hours) are calculated.

(3) The Experimental Results

The experimental results are shown in table 1. Table 1 shows that the acylated homoharringtonine derivatives of the present invention can induce cell death of human chronic myeloid leukemia cells, acute myeloid leukemia cells and acute lymphocytic leukemia cells, and inhibit the growth of these leukemia cells. Compared with homoharringtonine itself, the acylated homoharringtonine derivatives of the present invention exhibit significantly enhanced anti-leukemia cell activities. Specifically, the acylated homoharringtonine derivative of the present invention BS-HH-066 increase the anti-Kasumi-1 (acute myeloid leukemia M2 type, AML-M2) activity by more than 7-fold; BS-HH-074 improves the anti-K562/adr (drug-resistant, chronic myeloid leukemia, CML) activity by more than 5-fold, improves the anti-Kasumi-1 (acute myeloid leukemia M2 type, AML-M2) activity by more than 5-fold, and improves the anti-NB4 (acute promyelocytic leukemia, AML) and anti-H9 (acute lymphoblastic leukemia, ALL) activities by more than 2-fold. BS-HH-002 improves the anti-Kasumi-1 (acute myeloid leukemia M2 type, AML-M2) activity by more than 3.4-fold, improves the anti-K562/adr (drug-resistant, chronic myeloid leukemia, CML) activity by more than 3.2-fold, improves the anti-NB4 (acute promyelocytic leukemia, AML) activity by more than 3-fold, and improves the anti-H9 (acute lymphoblastic leukemia, ALL) activities by more than 5-fold.

TABLE 1

Determination of the inhibiting concentrations of the acylated homoharringtonine derivatives on leukemia cell growth (72 h, $IC_{50}$ (μg/mL) value and $IC_{90}$ (μg/mL) value).

| Compounds | K562/adr | | Kasumi-1 | | NB4 | |
|---|---|---|---|---|---|---|
| | $IC_{50}$ | $IC_{90}$ | $IC_{50}$ | $IC_{90}$ | $IC_{50}$ | $IC_{90}$ |
| HHT | 0.035 | 0.98 | 0.005 | 0.024 | 0.006 | 0.012 |
| BS-HH-001 | 0.062 | 1.18 | 0.006 | 0.021 | 0.01 | 0.022 |
| BS-HH-002 | 0.015 | 0.31 | 0.002 | 0.007 | 0.002 | 0.006 |
| BS-HH-0022 | 0.41 | 1.84 | 0.063 | 0.22 | 0.08 | 0.25 |
| BS-HH-0572 | 0.32 | 16 | 0.065 | 0.4 | 0.12 | 0.4 |
| BS-HH-059 | 0.03 | 0.35 | 0.005 | 0.012 | 0.006 | 0.012 |
| BS-HH-061 | 0.24 | 12.57 | 0.062 | 0.23 | 0.07 | 0.14 |
| BS-HH-062 | 0.06 | 0.75 | 0.002 | 0.005 | 0.004 | 0.007 |
| BS-HH-066 | 0.03 | 3.18 | 0.0007 | 0.002 | 0.002 | 0.004 |
| BS-HH-0721 | 0.01 | 0.05 | 0.002 | 0.004 | 0.003 | 0.005 |
| BS-HH-0722 | 0.9 | 3.72 | 0.14 | 0.47 | 0.2 | 0.49 |
| BS-HH-0732 | 2.5 | 6.5 | 1.35 | 3.56 | 1.19 | 2.47 |
| BS-HH-074 | 0.007 | 14.1 | 0.001 | 0.005 | 0.003 | 0.007 |
| BS-HH-076 | 0.02 | 0.21 | 0.006 | 0.023 | 0.009 | 0.022 |
| BS-HH-077 | 0.01 | 0.05 | 0.004 | 0.012 | 0.009 | 0.022 |

| Compounds | H9 | | Jurkat | |
|---|---|---|---|---|
| | $IC_{50}$ | $IC_{90}$ | $IC_{50}$ | $IC_{90}$ |
| HHT | 0.02 | 0.046 | 0.007 | 16 |
| BS-HH-001 | 0.02 | 0.05 | 0.012 | 16 |
| BS-HH-002 | 0.004 | 0.01 | 0.003 | 16 |
| BS-HH-0022 | 0.19 | 0.4 | 0.088 | 10.13 |
| BS-HH-0572 | 0.21 | 0.48 | 0.11 | 7.5 |
| BS-HH-059 | 0.007 | 0.02 | 0.003 | 16 |
| BS-HH-061 | 0.14 | 0.25 | 0.071 | 16 |
| BS-HH-062 | 0.008 | 0.02 | 0.012 | 16 |
| BS-HH-066 | 0.003 | 0.01 | 0.005 | 16 |
| BS-HH-0721 | 0.003 | 0.009 | 0.002 | 16 |
| BS-HH-0722 | 0.47 | 1.24 | 0.3 | 16 |
| BS-HH-0732 | 1.3 | 3.9 | 1.4 | 6.4 |
| BS-HH-074 | 0.004 | 0.01 | 0.0038 | 16 |
| BS-HH-076 | 0.01 | 0.04 | 0.006 | 6.24 |
| BS-HH-077 | 0.01 | 0.03 | 0.001 | 11.37 |

Example 5

Evaluation of the Anti-Human Multiple Myeloma and Lymphoma Cell Activities by the Homoharringtonine Derivatives of the Present Invention (1) Experimental Materials Multiple myeloma and lymphoma cell lines: RPMI8226 (multiple myeloma), purchased from Fuxiang Bio-tech Co. Ltd., Shanghai, China.

Reagents: the same as in Example 4.

Main apparatuses: a Thermo Scientific 3111 incubator and a Bio-Rad iMark microplate reader.

(2) Experimental Method

Obtaining 6000 well-growing leukemia cells and inoculating them into wells of a 96-well cell culture plate. The culture medium is the 1640 cell culture medium containing 10% fetal bovine serum. After adding the homoharringtonine derivatives of different concentrations and mixing uniformly, placing the plate in a carbon dioxide cell incubator (5% $CO_2$) at 37° C. and incubated for 72 hours. Then the viable cell concentration is determined by the MTT method. In this experiment, the cell viability in control group (not treated with any compound) is set as 100%. On such basis, the cell viability (%) after treatment and the 50% inhibiting concentration of the compound for the leukemia cell growth at 72 hours ($IC_{50}$ value of 72 hours) are calculated.

(3) The Experimental Results

The experimental results are shown in table 2. Table 2 shows that the acylated homoharringtonine derivatives of the present invention can induce cell death of human myeloma cells and lymphoma cells and inhibit the growth of these tumor cells. The acylated homoharringtonine derivatives, BS-HH-001 and BS-HH-002, of the present invention are particularly effective in anti-RPMI8226 (multiple myeloma).

Example 6

Evaluation of Anti-Human Solid Tumor Effect of the Acylated Homoharringtonine Derivatives of the Present Invention (1) Experimental Materials Human solid tumor cell lines: Hep-2 (laryngeal carcinoma), A549 (human lung cancer), CaES-17 (esophageal cancer cell), PC-3 (prostate cancer), CNE (nasopharyngeal carcinoma cell), and SK-OV-3 (ovarian cancer cell), all of which are purchased from China Center For Type Culture Collection; RKO (human colon adenocarcinoma cell), MGC 803 (human gastric cancer cell), MG63 (osteosarcoma) and U87 MG (malignant glioma cell), all of which are purchased from Fuxiang Bio-tech Co. Ltd., Shanghai, China; PANC-1 (pancreatic cancer), Huh7 (human liver cancer cell), Becap37 (human breast cancer cell), and Hela (human cervical cancer cell), all of which are donated by Cancer Research Institute of Zhejiang University, China.

Reagents: the same as in Example 4.

Main apparatuses: a Thermo Scientific 3111 incubator and a Bio-Rad iMark microplate reader.

(2) Experimental Method

Obtaining 4000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. and incubated for 24 hours. After adding the homoharringtonine derivatives of different concentration and mixing uniformly, the plate is placed in a carbon dioxide cell incubator (5% $CO_2$) at 37° C. and incubated for 72 hours. Then the viable cell concentration is determined by the MTT method and the cell viability (%) after drug treatment is calculated. In this experiment, the cell viability of control group (not treated with any compound) is set as 100%.

(3) The Experimental Results are Shown in Table 2.

Table 2 shows that the acylated homoharringtonine derivatives of the present invention can induce cell death of human myeloma cell and lymphoma cell and inhibit the growth of these tumor cells. Specifically, the anti-RPMI8226 (multiple myeloma) effect of the inventive acylated homoharringtonine derivatives BS-HH-002, BS-HH-0721 and BS-HH-074 is more than 2-fold of that of homoharringtonine. The anti-A549 (human lung cancer) effect of BS-HH-002, BS-HH-0721 and BS-HH-074 is more than 3-fold of that of homoharringtonine. The anti-PANC-1 (pancreatic cancer) effect of BS-HH-002 and BS-HH-0721 is more than 3-fold and 4-fold of that of homoharringtonine, respectively. The anti-Becap37 (human breast cancer cell) effect of BS-HH-002, BS-HH-059, BS-HH-0721 and BS-HH-074 is more than 2-fold of that of homoharringtonine. The anti-MG63 (osteosarcoma) effect of BS-HH-002, BS-HH-059, BS-HH-0721 and BS-HH-074 is substantially superior to that of homoharringtonine. The anti-Huh7 (human liver cancer cell) effect of BS-HH-002 and BS-HH0721 is more than 2-fold of that of homoharringtonine. The anti-RKO (human colon adenocarcinoma cell) effect of BS-HH-002, BS-HH-059 and BS-HH-0721 is substantially superior to that of homoharringtonine. The anti-Hela (human cervical cancer cell) effect of BS-HH-002, BS-HH-0721 and BS-HH-074 is more than 2.5-fold, 4.0-fold, and 5.6-fold of that of homoharringtonine, respectively. The anti-CaES-17 (esophageal cancer cell) effect of BS-HH-002 and BS-HH-0721 is more than 2-fold of that of homoharringtonine. The anti-CNE (nasopharyngeal carcinoma cell) effect of BS-HH-0721, BS-HH-074 and BS-HH077 is more than 10-fold, 27-fold, and 3-fold of that of homoharringtonine, respectively. The anti-Hep-2 (laryngeal carcinoma) effect of BS-HH-002, BS-HH-0721, BS-HH074 and BS-HH-077 is more than 2-fold of that of homoharringtonine. The anti-PC-3 (prostate cancer) effect of BS-HH-002 and BS-HH-074 is more than 6-fold and 10-fold of that of homoharringtonine, respectively. The anti-SK-OV-3 (ovarian cancer cell) effect of BS-HH-002 is 2-fold of that of homoharringtonine.

TABLE 2

Determination of the half inhibiting concentrations of the acylated homoharringtonine derivatives on lymphoma, multiple myeloma and human solid tumor cell growth (72 h, $IC_{50}$ (μg/mL) value and $IC_{90}$ (μg/mL) value).

| Compounds | RPMI8226 | | A549 | | PANC-1 | |
|---|---|---|---|---|---|---|
| | $IC_{50}$ | $IC_{90}$ | $IC_{50}$ | $IC_{90}$ | $IC_{50}$ | $IC_{90}$ |
| HHT | 0.006 | 0.027 | 0.03 | >16 | 0.035 | >16 |
| BS-HH-001 | 0.009 | 0.12 | 0.03 | >16 | 0.036 | >16 |
| BS-HH-002 | 0.003 | 0.018 | 0.013 | >16 | 0.012 | >16 |
| BS-HH-0022 | 0.12 | 0.63 | 0.23 | >16 | 0.69 | 15.56 |
| BS-HH-0572 | 0.155 | 1.13 | 0.48 | >16 | 0.43 | 12.56 |
| BS-HH-059 | 0.006 | 0.039 | 0.03 | >16 | 0.029 | >16 |
| BS-HH-061 | 0.062 | 0.25 | 0.52 | >16 | 0.21 | >16 |
| BS-HH-062 | 0.007 | 0.029 | 0.04 | >16 | 0.044 | >16 |

TABLE 2-continued

Determination of the half inhibiting concentrations of the acylated homoharringtonine derivatives on lymphoma, multiple myeloma and human solid tumor cell growth (72 h, $IC_{50}$ (μg/mL) value and $IC_{90}$ (μg/mL) value).

| | | | | | | |
|---|---|---|---|---|---|---|
| BS-HH-066 | 0.006 | 0.033 | 0.03 | >16 | 0.026 | >16 |
| BS-HH-0721 | 0.002 | 0.014 | 0.01 | >16 | 0.009 | >16 |
| BS-HH-0722 | 0.29 | 1.82 | 0.89 | >16 | 0.83 | >16 |
| BS-HH-0732 | 1.15 | 3.84 | 5.4 | >16 | 5.8 | 16 |
| BS-HH-074 | 0.003 | 0.015 | 0.007 | >16 | 0.014 | >16 |
| BS-HH-076 | 0.007 | 0.034 | 0.03 | >16 | 0.042 | >16 |
| BS-HH-077 | 0.004 | 0.024 | 0.02 | >16 | 0.055 | >16 |

| | Becap37 | | MG 63 | | Huh7 | | RKO | |
|---|---|---|---|---|---|---|---|---|
| Compounds | $IC_{50}$ | $IC_{90}$ | $IC_{50}$ | $IC_{90}$ | $IC_{50}$ | $IC_{90}$ | $IC_{50}$ | $IC_{90}$ |
| HHT | 0.01 | 11.56 | 0.01 | 1.2 | 0.004 | 0.049 | 0.003 | 0.009 |
| BS-HH-001 | 0.015 | 13.96 | 0.02 | 2.4 | 0.016 | 0.13 | 0.007 | 0.02 |
| BS-HH-002 | 0.005 | 16 | 0.006 | 0.42 | 0.0021 | 0.018 | 0.002 | 0.01 |
| BS-HH-0022 | 0.23 | 11.14 | 0.24 | 3.25 | 0.13 | 0.99 | 0.044 | 0.35 |
| BS-HH-0572 | 0.2 | 9.75 | 0.2 | 4.75 | 0.17 | 1.7 | 0.12 | 0.56 |
| BS-HH-059 | 0.007 | 7.4 | 0.02 | 3.08 | 0.012 | 0.081 | 0.001 | 0.015 |
| BS-HH-061 | 0.17 | 16 | 0.093 | 10.76 | 0.056 | 0.34 | 0.039 | 0.24 |
| BS-HH-062 | 0.014 | 15.61 | 0.012 | 0.77 | 0.004 | 0.049 | 0.005 | 0.025 |
| BS-HH-066 | 0.02 | 5.63 | 0.0032 | 0.2 | 0.0016 | 0.023 | 0.003 | 0.023 |
| BS-HH-0721 | 0.003 | 8.17 | 0.006 | 0.44 | 0.0022 | 0.038 | 0.0009 | 0.005 |
| BS-HH-0722 | 0.47 | 16 | 0.21 | 9.43 | 0.66 | 7.6 | 0.22 | 0.87 |
| BS-HH-0732 | 2.9 | 12.7 | 1.34 | 9.88 | 4.8 | 14.5 | 1.4 | 5.24 |
| BS-HH-074 | 0.003 | 8.38 | 0.006 | 1.18 | 0.003 | 0.05 | 0.002 | 0.006 |
| BS-HH-076 | 0.01 | 6.4 | 0.022 | 1.72 | 0.008 | 0.096 | 0.008 | 0.02 |
| BS-HH-077 | 0.007 | 11.12 | 0.021 | 5.14 | 0.016 | 0.36 | 0.006 | 0.02 |

| | U87 MG | | Hela | | CaES-17 | | CNE | |
|---|---|---|---|---|---|---|---|---|
| Compounds | $IC_{50}$ | $IC_{90}$ | $IC_{50}$ | $IC_{90}$ | $IC_{50}$ | $IC_{90}$ | $IC_{50}$ | $IC_{90}$ |
| HHT | 0.004 | 0.018 | 0.019 | 16 | 0.037 | >16 | 0.038 | >16 |
| BS-HH-001 | 0.018 | 0.11 | 0.026 | >16 | 0.062 | >16 | 0.062 | >16 |
| BS-HH-002 | 0.002 | 0.012 | 0.0077 | 16 | 0.02 | >16 | 0.024 | >16 |
| BS-HH-0022 | 0.16 | 0.59 | 0.33 | 9.38 | 0.61 | >16 | 0.21 | 16 |
| BS-HH-0572 | 0.23 | 0.99 | 0.45 | 11.54 | 0.74 | 16 | 0.35 | 14.28 |
| BS-HH-059 | 0.023 | 0.18 | 0.014 | 16 | 0.029 | 16 | 0.031 | >16 |
| BS-HH-061 | 0.31 | 0.96 | 0.31 | 16 | 0.38 | 16 | 0.42 | >16 |
| BS-HH-062 | 0.02 | 0.1 | 0.026 | 16 | 0.058 | 16 | 0.028 | >16 |
| BS-HH-066 | 0.007 | 0.048 | 0.021 | 16 | 0.049 | 16 | 0.03 | >16 |
| BS-HH-0721 | 0.008 | 0.07 | 0.005 | 16 | 0.014 | 16 | 0.0037 | >16 |
| BS-HH-0722 | 0.67 | 3.42 | 0.87 | >16 | 1.24 | 16 | 0.77 | >16 |
| BS-HH-0732 | 2 | 8.54 | 2.61 | 8.37 | 3.93 | 16 | 3.91 | >16 |
| BS-HH-074 | 0.012 | 0.08 | 0.0034 | 12.59 | 0.015 | 16 | 0.0014 | >16 |
| BS-HH-076 | 0.009 | 0.067 | 0.011 | 10.25 | 0.039 | 16 | 0.029 | >16 |
| BS-HH-077 | 0.035 | 0.16 | 0.014 | 16 | 0.031 | 16 | 0.012 | >16 |

| | Hep-2 | | MGC 803 | | PC-3 | | SK-OV-3 | |
|---|---|---|---|---|---|---|---|---|
| Compounds | $IC_{50}$ | $IC_{90}$ | $IC_{50}$ | $IC_{90}$ | $IC_{50}$ | $IC_{90}$ | $IC_{50}$ | $IC_{90}$ |
| HHT | 0.014 | >16 | 0.016 | 0.2 | 0.08 | >16 | 0.09 | >16 |
| BS-HH-001 | 0.026 | >16 | 0.03 | 0.66 | 0.029 | >16 | 0.12 | >16 |
| BS-HH-002 | 0.0037 | >16 | 0.008 | 0.056 | 0.013 | >16 | 0.05 | >16 |
| BS-HH-0022 | 0.22 | >16 | 0.16 | 0.76 | 1.37 | >16 | 1.33 | >16 |
| BS-HH-0572 | 0.23 | >16 | 0.24 | 1.62 | 1.84 | >16 | 0.98 | >16 |
| BS-HH-059 | 0.015 | >16 | 0.021 | 0.11 | 0.08 | >16 | 0.08 | >16 |
| BS-HH-061 | 0.39 | >16 | 0.058 | 0.16 | 3.15 | >16 | 0.4 | >16 |
| BS-HH-062 | 0.015 | >16 | 0.015 | 0.07 | 0.11 | >16 | 0.12 | >16 |
| BS-HH-066 | 0.025 | >16 | 0.005 | 0.052 | 0.1 | >16 | 0.051 | >16 |
| BS-HH-0721 | 0.004 | >16 | 0.006 | 0.019 | 0.04 | >16 | 0.022 | >16 |
| BS-HH-0722 | 0.48 | >16 | 0.5 | 12 | 0.82 | >16 | 1.94 | >16 |
| BS-HH-0732 | 3.46 | >16 | 2.7 | 9.92 | 3.97 | 16 | 6.71 | >16 |
| BS-HH-074 | 0.006 | >16 | 0.006 | 0.055 | 0.0077 | >16 | 0.027 | >16 |
| BS-HH-076 | 0.012 | >16 | 0.025 | 0.098 | 0.03 | >16 | 0.031 | >16 |
| BS-HH-077 | 0.007 | >16 | 0.021 | 0.087 | 0.039 | >16 | 0.034 | >16 |

Example 7

Evaluation of the In Vivo Anti-Tumor Activity and Preliminary Evaluation of the Toxicity of the Acylated Homoharringtonine Derivative BS-HH-002 of the Present Invention

Experiment 7-1

The Inhibition of BS-HH-002 on the Transplanted Tumor of Leukemia in NOD/SCID Mice (1) Experimental Materials Leukemia cell lines: Kasumi-1 (acute myeloid leukemia M2 type, AML-M2)

Animal: NOD/SCID mice (multiple immunodeficiency mice), 8 weeks, female, purchased from Shanghai Laboratory Animal Center of Chinese Academy of Sciences, China.

(2) Reagents:

BS-HH-002, wherein BS-HH-002-0.1 indicates a dosage of 0.1 mg/kg each time, and BS-HH-002-0.3 indicates a dosage of 0.3 mg/kg each time.

(3) Main Apparatuses:

an incubator, a clean bench and a laminar flow rack.

(4) Experimental Method

Under sterile conditions, the above tumor cells in the logarithmic growth phase are collected and injected in an amount of $5 \times 10^7/0.2$ ml/mice (cell viability>95%) by subcutaneous injection into the right subaxillary of NOD/SCID mice, thus establishing an NOD/SCID mice model bearing transplanted tumor of leukemia. The mice are administered on the third day after the inoculation, wherein the experimental groups are intragastrically administered in an experimentally designed amount and the negative control group is intragastrically administered with sterile water. Each mouse is intragastrically administered three times a day in 0.4 ml each time, at 8:00, 14:00 and 20:00 with 6-hour intervals, and is successively administered for 10 days. The day before administration is Day 0 and the weight and tumor size are determined approximately every 5 days to produce a dynamic plot on weight and tumor growth. On Day 31, the mice are dissected and the tumors are taken out and weighed. The tumor inhibition rate (%) after the application of medicament is determined based on the tumor inhibition rate of the control group being zero.

The values determined are presented as mean±standard error (M±SD). The experimental data for each group are analyzed by the One-way ANOVA method of SPSS 18.0 Statistical Software, and $p<0.05$ is deemed as having statistically significant difference.

Figure 4:
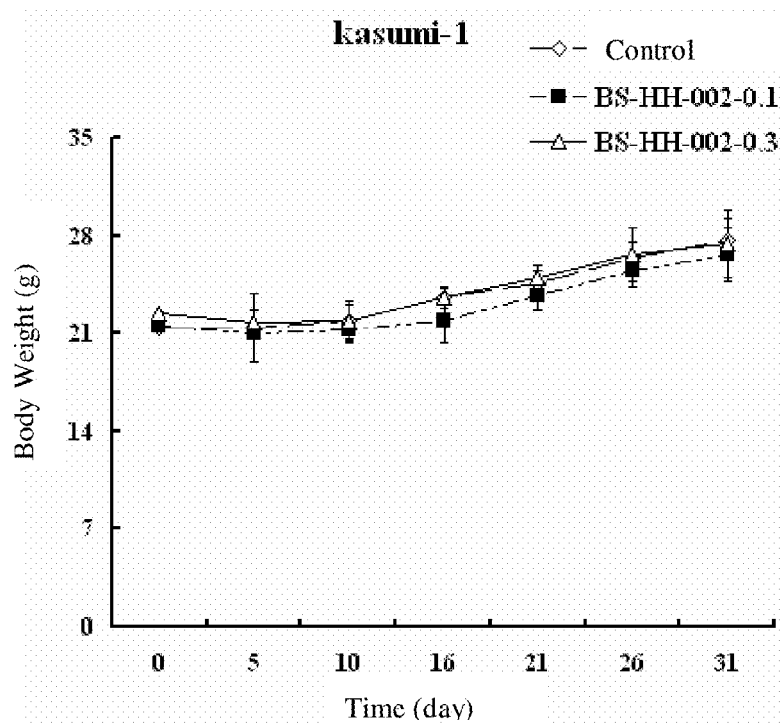
FIG. 4 is a plot showing the dynamic changes of the effect of BS-HH-002 on the weight of NOD/SCID mice.

As is shown in FIG. 4, the control group and the experimental groups do not demonstrate distinct differences in body weight, and no obvious signs of physical change are observed for the animals. These indicate that BS-HH-002 does not have any obvious toxic or side effect under the two given dosages.

Figure 5:
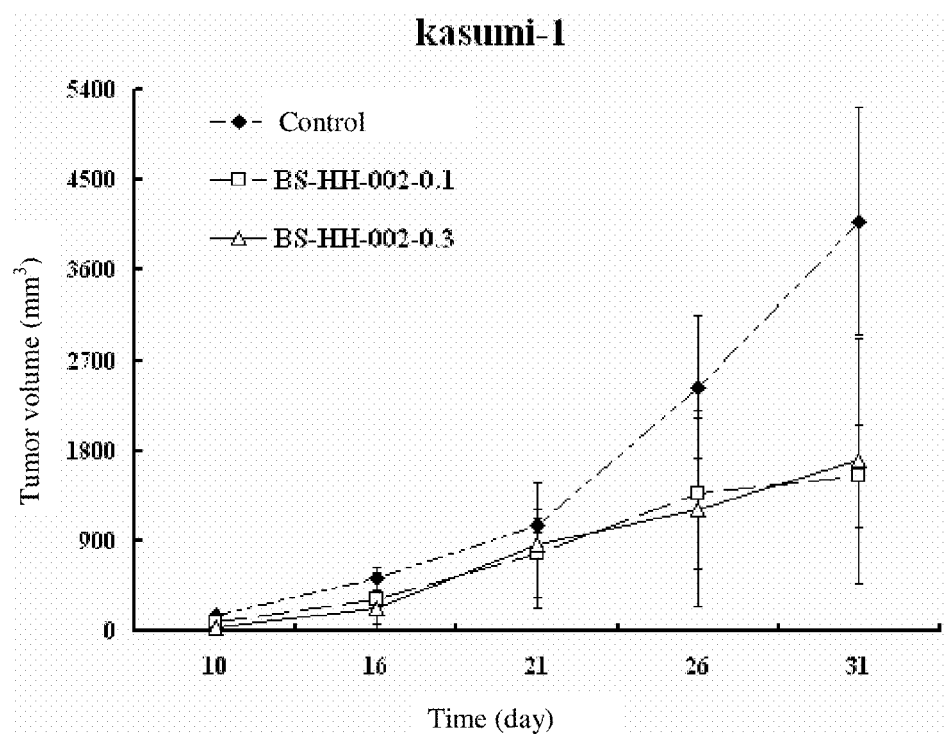
FIG. 5 shows a curve depicting the effect of BS-HH-002 on the transplanted tumor of leukemia in NOD/SCID mice.

FIG. 5 is a curve showing the effect of BS-HH-002 on the transplanted tumor of leukemia in NOD/SCID mice. As is shown in FIG. 5, BS-HH-002 presents remarkable tumor inhibition effect but does not demonstrate obvious dependency on the dosage.

Figure 6:
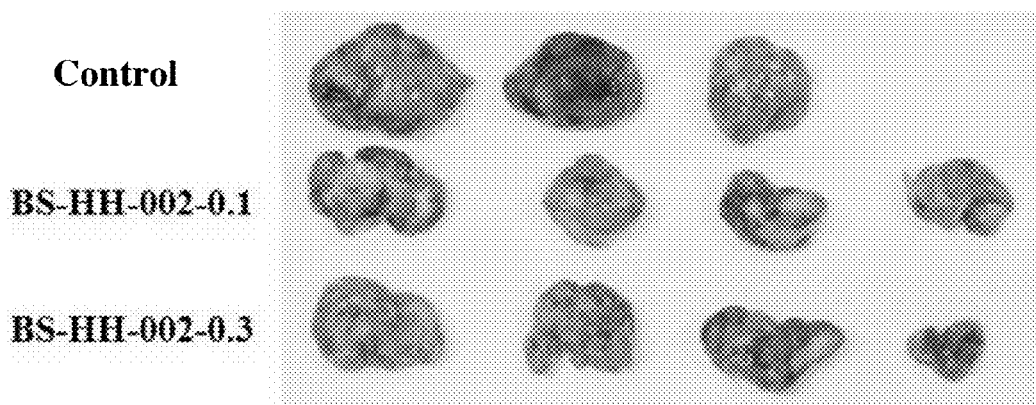
FIG. 6 shows the effect of BS-HH-002 on the weight of the transplanted tumor of leukemia in NOD/SCID mice.

FIG. 6 shows that BS-HH-002 has substantially reduced the weight of the transplanted tumor of leukemia in NOD/SCID mice.

Figure 7:
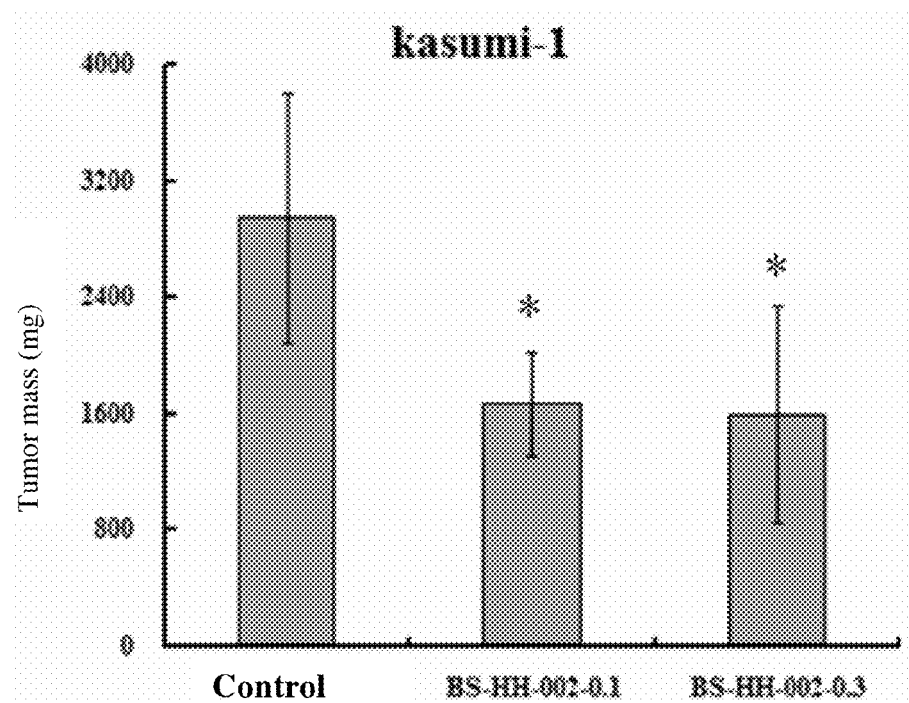
FIG. 7 shows the effect of BS-HH-002 on the weight of the transplanted tumor of leukemia in NOD/SCID mice, wherein * indicates p<0.05 as compared with the control group.

FIG. 7 shows the effect of BS-HH-002 on the weight of the transplanted tumor of leukemia in NOD/SCID mice.

Figure 8:
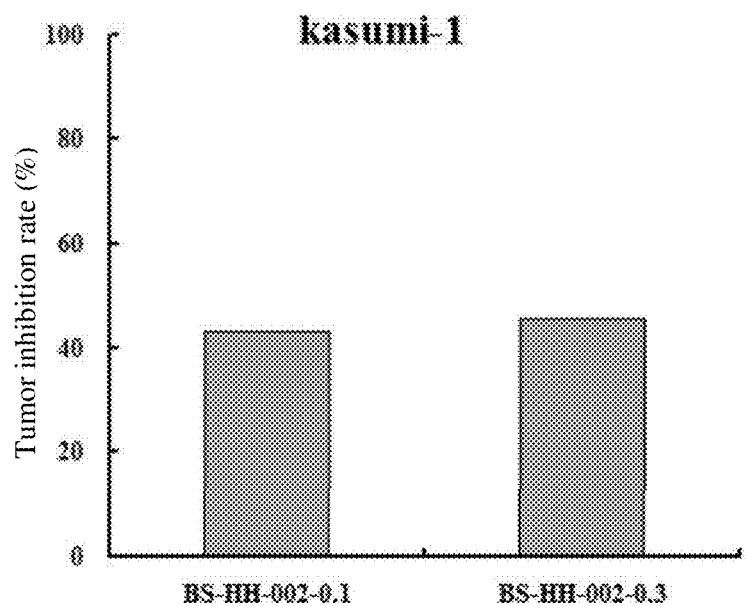
FIG. 8 shows the inhibition on transplanted tumor of leukemia in NOD/SCID mice by BS-HH-002.

FIG. 8 shows the inhibition of transplanted tumor of leukemia in NOD/SCID mice by BS-HH-002.

As is shown in the above table and figures, in the in vivo animal experiments, BS-HH-002 has an inhibition rate of over 40% of transplanted tumor of leukemia under the dosage of both 0.1 and 0.3 mg/kg. In view of the initial and final weight, BS-HH-002 does not have substantial impact on animal weight and does not demonstrate an obvious toxicity.

Experiment 7-2

The Inhibition of BS-HH-002 on the Transplanted Tumor of Gastric Cancer in BALB/c-nu Nude Mice (1) Experimental Materials Gastric cancer cell lines: MGC-803

Animal: BALB/c-nu nude mice, 8 weeks, female, purchased from Shanghai Laboratory Animal Center of Chinese Academy of Sciences, China.

(2) Reagents:

BS-HH-002, wherein BS-HH-002-0.1 indicates a dosage of 0.1 mg/kg each time, BS-HH-002-0.3 indicates a dosage of 0.3 mg/kg each time, BS-HH-002-0.5 indicates a dosage of 0.5 mg/kg each time, and BS-HH-002-1.0 indicates a dosage of 1.0 mg/kg each time.

(3) Main Apparatuses:

an incubator, a clean bench and a laminar flow rack.

(4) Experimental Method

Under sterile conditions, the above tumor cells in logarithmic growth phase are collected and injected in an amount of $2 \times 10^7/0.2$ ml/nude mice (cell viability>95%) into the

TABLE 3

The effect of BS-HH-002 on transplanted tumors of in NOD/SCID mice

| Group | Dosage (mg/kg/time) | Number of Animals | | Weight (g) | | Mass of tumor (g) | Tumor Inhibition rate (%) |
|---|---|---|---|---|---|---|---|
| | | Initial | Final | Initial | Final | | |
| Control | — | 3 | 3 | 21.37 ± 0.12 | 27.7 ± 1.47 | 2.95 ± 0.86 | — |
| BS-HH-002-0.1 | 0.1 | 4 | 4 | 21.48 ± 0.05 | 26.7 ± 1.92 | 1.67 ± 0.36* | 43.31 |
| BS-HH-002-0.3 | 0.3 | 4 | 4 | 22.45 ± 0.13 | 27.45 ± 2.48 | 1.60 ± 0.75* | 45.74 |

Note:
as compared with the control group, * indicates P < 0.05.

right subaxillary of the nude mice by subcutaneous injection, thus establishing a BALB/c-nu nude mice model bearing transplanted tumor of gastric cancer. The mice are administered on the third day after the inoculation, wherein the experimental groups are intragastrically administered in an experimentally designed amount, and the negative control group is intragastrically administered with sterile water. Each mouse is intragastrically administered in 0.4 ml each time in a dosing regime as listed in Table 4. Administration takes place at 8:00 for one time a day, at 8:00 and 14:00 for twice a day, and at 8:00, 14:00 and 20:00 with 6-hour intervals for three times day. The administrations are successive for 10 days. The day before administration is Day 0 and the weight and tumor size are determined approximately every 5 days to produce a plot on weight and tumor growth. On Day 27, the mice are dissected and the tumors are taken out and weighed. Based on a tumor inhibition rate of zero for the control group, the tumor inhibition rate (%) after the effect of the medicament is calculated.

The values determined are presented as mean±standard error (M±SD). The experimental data for each group are analyzed by the One-way ANOVA method of SPSS 18.0 Statistical Software, and p<0.05 is deemed as having statistically significant difference.

As is shown in the above figures, in the in vivo experiments, BS-HH-002 has a tumor inhibition rate of more than 40% on gastric cancer. The mass of tumor shows a substantial difference as compared with the control group (P<0.05), wherein the experimental group having a dosing regime of 3 times a day for 1.0 mg/kg each time demonstrates extremely distinct difference as compared with the control group (P<0.01). Furthermore, in view of the initial and final weight, both the administered groups and the control group demonstrate an obvious increase in weight with an essentially identical tendency. Additionally, none of the animals has died in any group therein until dissection. These indicate that none of the dosages causes obvious toxic and side effect on the animals.

The invention claimed is:
1. An acylated homoharringtonine compound of formula (I) or formula (II):

TABLE 4

The effect of BS-HH-002 on transplanted tumors of gastric cancer in BALB/c-nu nude mice

| Group | Dosage (mg/kg/ time) | Frequency (time/ day) | Number of Anmial | | Weight (g) | | Mass of tumor (g) | Tumor Inhibition rate (%) |
|---|---|---|---|---|---|---|---|---|
| | | | Initial | Final | Initial | Final | | |
| Control | — | 3 | 4 | 4 | 23.88 ± 0.32 | 28.48 ± 0.75 | 0.78 ± 0.52* | — |
| BS-HH-002-0.1 | 0.1 | 1 | 4 | 4 | 18.88 ± 0.56 | 27.18 ± 3.62 | 0.40 ± 0.18* | 48.97 |
| BS-HH-002-0.3 | 0.3 | 1 | 4 | 4 | 18.98 ± 0.51 | 24.30 ± 1.38 | 0.38 ± 0.13* | 51.76 |
| BS-HH-002-0.5 | 0.5 | 1 | 4 | 4 | 20.10 ± 0.22 | 25.78 ± 1.15 | 0.44 ± 0.13* | 43.81 |
| BS-HH-002-1.0 | 1.0 | 1 | 4 | 4 | 20.45 ± 0.76 | 25.95 ± 0.94 | 0.43 ± 0.17* | 44.58 |
| BS-HH-002-0.1 | 0.1 | 2 | 4 | 4 | 21.35 ± 0.34 | 25.63 ± 1.06 | 0.46 ± 0.11* | 40.90 |
| BS-HH-002-0.5 | 0.5 | 2 | 4 | 4 | 22.28 ± 0.43 | 26.68 ± 1.42 | 0.44 ± 0.18* | 43.43 |
| BS-HH-002-0.1 | 0.1 | 3 | 4 | 4 | 24.58 ± 0.39 | 28.50 ± 2.83 | 0.41 ± 0.09* | 48.14 |
| BS-HH-002-0.5 | 0.5 | 3 | 4 | 4 | 23.50 ± 0.37 | 26.33 ± 2.76 | 0.37 ± 0.18* | 52.12 |
| BS-HH-002-1.0 | 1.0 | 3 | 4 | 4 | 26.98 ± 0.75 | 29.98 ± 1.32 | 0.34 ± 0.05** | 56.67 |

Note:
as compared with the control group, * indicates that P < 0.05 and ** indicates P < 0.01.

Figure 9:
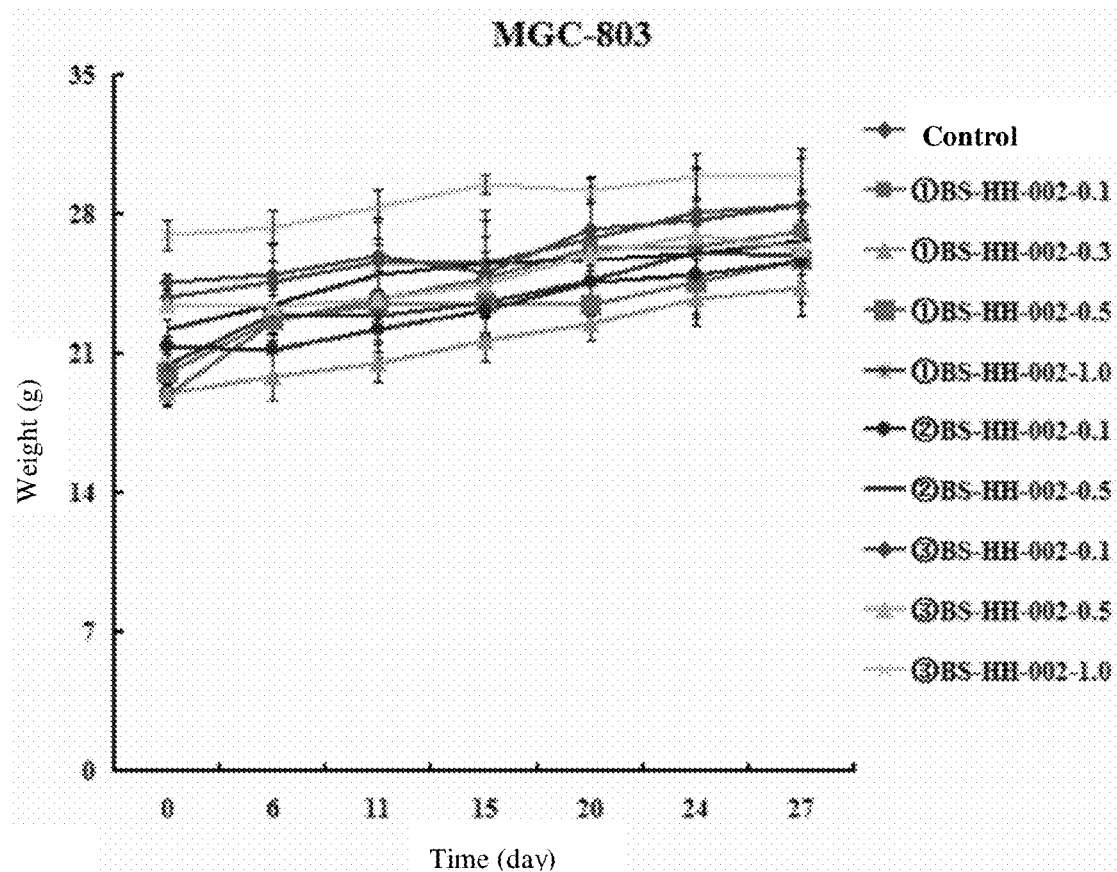
FIG. 9 shows the curves depicting the effect of BS-HH-002 on the weight of BALB/c-nu nude mice.

FIG. 9 shows a curve illustrating the effect of BS-HH-002 on the body weight of BALB/c-nu nude mice.

Figure 10:
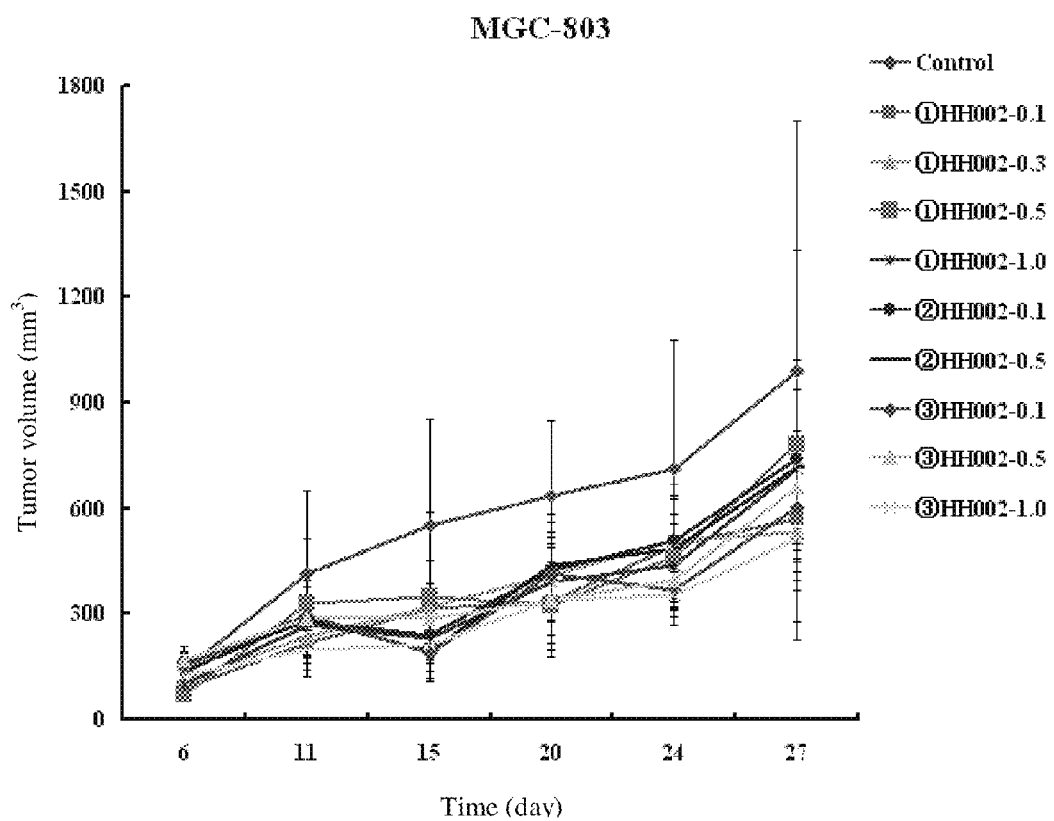
FIG. 10 shows the curves depicting the effect of BS-HH-002 on transplanted gastric tumor of BALB/c-nu nude mice.

FIG. 10 shows a curve illustrating that BS-HH-002 affects the transplanted tumor of gastric cancer in BALB/c-nu nude mice.

Figure 11:
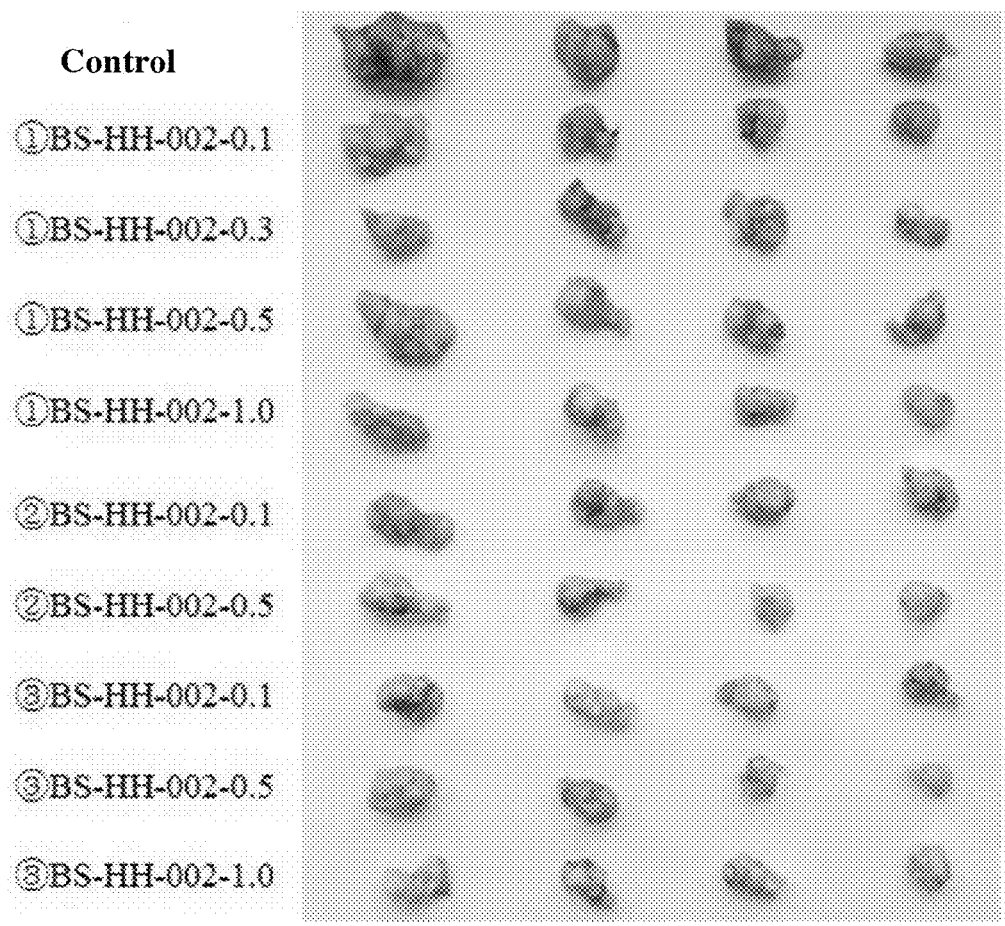
FIG. 11 shows the effect of BS-HH-002 on the weight of the transplanted tumor of gastric cancer in BALB/c-nu nude mice.

FIG. 11 shows the effect of BS-HH-002 on the weight of the transplanted tumor of gastric cancer in BALB/c-nu nude mice.

Figure 12:
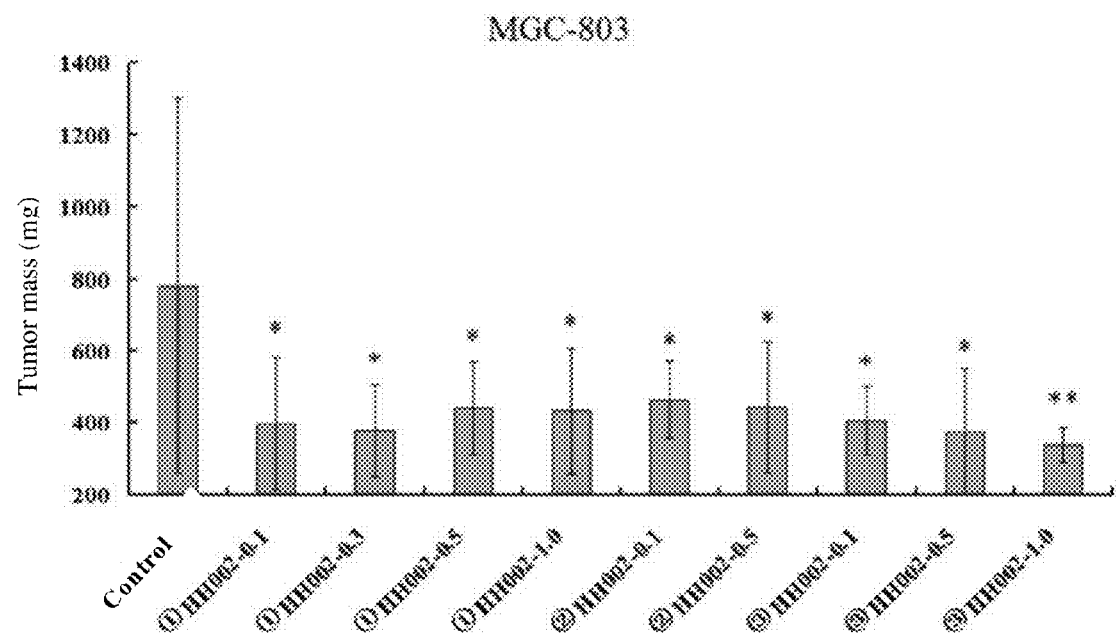
FIG. 12 shows the effect of BS-HH-002 on the weight of the transplanted tumor of gastric cancer in BALB/c-nu nude mice, wherein * indicates p<0.05 and ** indicates p<0.01 as compared with the control group.

FIG. 12 shows the effect of BS-HH-002 on the weight of the transplanted tumor of gastric cancer in BALB/c-nu nude mice.

Figure 13:
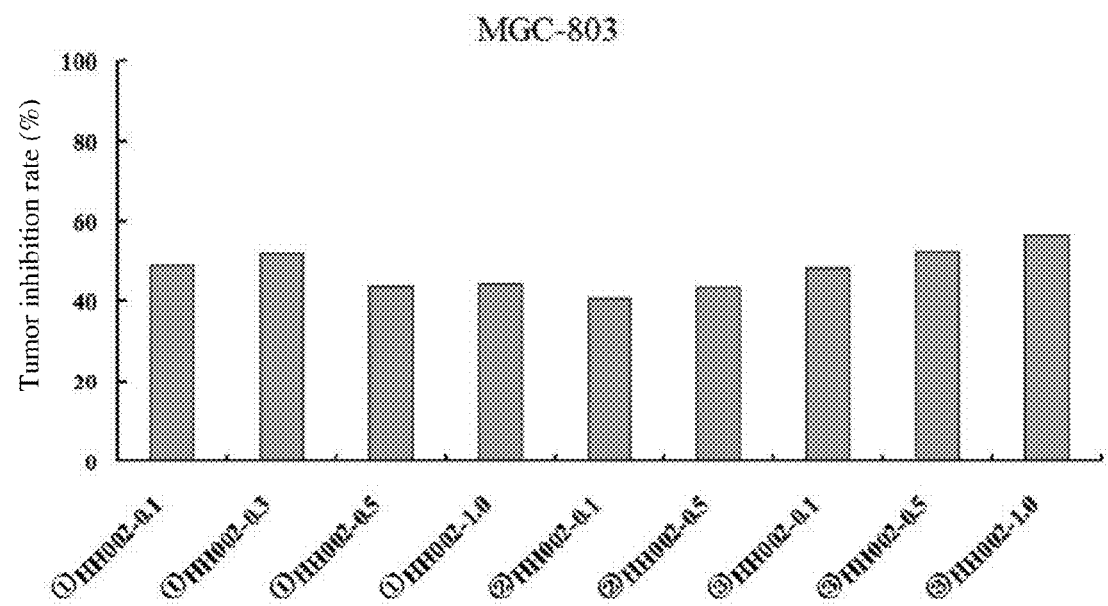
FIG. 13 shows the inhibition on the transplanted tumor of gastric cancer in BALB/c-nu nude mice by BS-HH-002.

FIG. 13 shows the inhibition of the transplanted tumor of gastric cancer in BALB/c-nu nude mice by BS-HH-002.

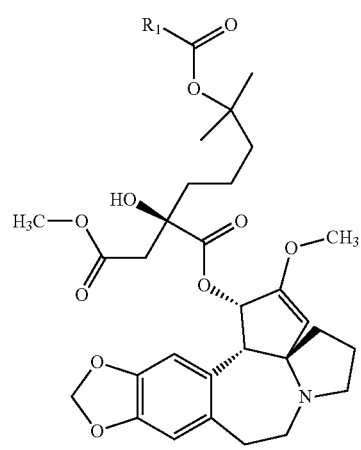

-continued

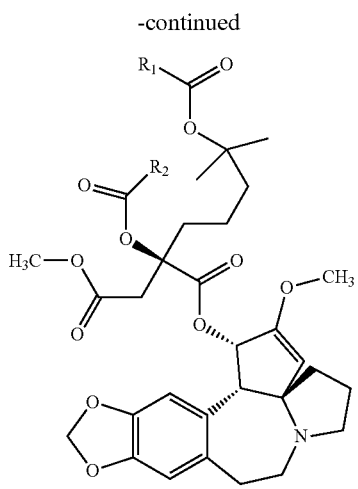

or a pharmaceutically acceptable salt thereof;
wherein
R₁ and R₂ are independently selected from H, $C_1$-$C_{20}$ alkyl, $C_2$-$C_{20}$ alkenyl, $C_4$-$C_{20}$ conjugated alkenyl, $C_3$-$C_7$ cycloalkyl or cycloalkenyl, aryl, heterocyclyl, heteroaryl, and amino acid side chain residues, which, except for H, are optionally substituted with one or more substituents selected from the group consisting of halogen, amino, $C_1$-$C_6$ alkyl amino, nitro, cyano, hydroxyl, $C_1$-$C_6$ alkoxy, thiol and $C_1$-$C_6$ alkylthio;
said $C_3$-$C_7$ cycloalkyl or cycloalkenyl, aryl, heterocyclyl or heteroaryl are further optionally substituted with $C_1$-$C_6$ alkyl; and
said $C_1$-$C_{20}$ alkyl, $C_2$-$C_{20}$ alkenyl or $C_4$-$C_{20}$ conjugated alkenyl are further optionally substituted with aryl or heteroaryl.

2. The acylated homoharringtonine compound of claim 1, or a pharmaceutically acceptable salt thereof, wherein
R₁ and R₂ are independently selected from H, $C_1$-$C_6$ alkyl, $C_2$-$C_6$ alkenyl, $C_4$-$C_8$ conjugated alkenyl, $C_3$-$C_7$ cycloalkyl or cycloalkenyl, aryl, heterocyclyl, heteroaryl and amino acid side chain residues, which, except for H, are optionally substituted with one or more substituents selected from the group consisting of halogen, amino, $C_1$-$C_4$ alkyl amino, nitro, cyano, hydroxyl, $C_1$-$C_4$ alkoxy, thiol and $C_1$-$C_4$ alkylthio;
said $C_3$-$C_7$ cycloalkyl or cycloalkenyl, aryl, heterocyclyl or heteroaryl are further optionally substituted with $C_1$-$C_4$ alkyl; and
said $C_1$-$C_6$ alkyl, $C_2$-$C_6$ alkenyl or $C_4$-$C_8$ conjugated alkenyl are further optionally substituted with aryl or heteroaryl.

3. The acylated homoharringtonine compound of claim 1, or a pharmaceutically acceptable salt thereof, wherein
R₁ and R₂ are independently selected from $C_1$-$C_6$ alkyl, $C_2$-$C_6$ alkenyl, $C_3$-$C_7$ cycloalkyl, aryl and heteroaryl, which are optionally substituted with one or more substituents selected from the group consisting of halogen, amino, $C_1$-$C_4$ alkylamino, nitro, cyano, hydroxyl, $C_1$-$C_4$ alkoxy, thiol and $C_1$-$C_4$ alkylthio;
said $C_3$-$C_7$ cycloalkyl, aryl and heteroaryl are further optionally substituted with $C_1$-$C_4$ alkyl; and
said $C_1$-$C_6$ alkyl or $C_2$-$C_6$ alkenyl are further optionally substituted with aryl or heteroaryl.

4. The acylated homoharringtonine compound of claim 1, or a pharmaceutically acceptable salt thereof, wherein R₁ and R₂ are independently selected from the group consisting of a $C_1$-$C_6$ alkyl, a $C_1$-$C_6$ alkyl substituted with aryl or heteroaryl, a $C_2$-$C_6$ alkenyl, a $C_2$-$C_6$ alkenyl substituted with aryl or heteroaryl, a $C_3$-$C_7$ cycloalkyl, an aryl, an aryl substituted with $C_1$-$C_4$ alkyl, a heteroaryl and a heteroaryl substituted with $C_1$-$C_4$ alkyl, each of which are optionally substituted with one or more substituents selected from the group consisting of halogen, amino, $C_1$-$C_4$ alkyl amino, nitro, cyano, hydroxyl, $C_1$-$C_4$ alkoxy, thiol and $C_1$-$C_4$ alkylthio.

5. The acylated homoharringtonine compound of claim 1, or a pharmaceutically acceptable salt thereof, wherein R₁ and R₂ are independently selected from the group consisting of a $C_1$-$C_6$ alkyl, a $C_1$-$C_6$ alkyl substituted with aryl or heteroaryl, a $C_2$-$C_6$ alkenyl, a $C_2$-$C_6$ alkenyl substituted with aryl or heteroaryl, a $C_3$-$C_7$ cycloalkyl, aryl, an aryl substituted with $C_1$-$C_4$ alkyl, a heteroaryl and a heteroaryl substituted with $C_1$-$C_4$ alkyl, each of which is optionally substituted with one or more halogen atoms.

6. The acylated homoharringtonine compound of claim 1, or a pharmaceutically acceptable salt thereof, wherein
said aryl is phenyl;
said heteroaryl is furanyl, thiophenyl, pyridinyl, oxazolyl or isoxazolyl;
said $C_3$-$C_7$ cycloalkyl is cyclopropyl, cyclobutyl, cyclopentyl or cyclohexyl; and
wherein each aryl, heteroaryl or $C_3$-$C_7$ cycloalkyl is optionally substituted with $C_1$-$C_4$ alkyl or halogen.

7. The acylated homoharringtonine compound of claim 6, or a pharmaceutically acceptable salt thereof, wherein
said aryl is phenyl;
said heteroaryl is furanyl, thiophenyl, pyridinyl, oxazolyl or isoxazolyl;
said $C_3$-$C_7$ cycloalkyl is cyclopropyl, cyclobutyl, cyclopentyl or cyclohexyl; and
wherein each aryl, heteroaryl, or $C_3$-$C_7$ cycloalkyl is optionally substituted with methyl, chlorine or bromine.

8. The acylated homoharringtonine compound of claim 1, or a pharmaceutically acceptable salt thereof, which is a compound of formula (I) or a pharmaceutically acceptable salt thereof.

9. The acylated homoharringtonine compound of claim 8, or a pharmaceutically acceptable salt thereof, wherein R₁ is selected from the group consisting of a $C_1$-$C_6$ alkyl, a $C_1$-$C_6$ alkyl substituted with aryl or heteroaryl, a $C_3$-$C_7$ cycloalkyl, an aryl, an aryl substituted with $C_1$-$C_4$ alkyl, a heteroaryl and a heteroaryl substituted with $C_1$-$C_4$ alkyl, each of which is optionally substituted with one or more halogen atoms.

10. The acylated homoharringtonine compound of claim 9, or a pharmaceutically acceptable salt thereof, wherein
said aryl is phenyl;
said heteroaryl is furanyl, pyridinyl or thiazolyl;
said cycloalkyl is cyclopentyl; and
wherein each aryl, heteroaryl or cycloalkyl is optionally substituted with one or more halogen atoms.

11. The acylated homoharringtonine compound of claim 10, or a pharmaceutically acceptable salt thereof, wherein R₁ is selected from the group consisting of methyl, furanyl, pyridinyl optionally substituted with halogen, thiazolyl optionally substituted with methyl, phenyl, and cyclopentyl.

12. The acylated homoharringtonine compound of claim 1, or a pharmaceutically acceptable salt thereof, which is a compound selected from the group consisting of BS-HH-001
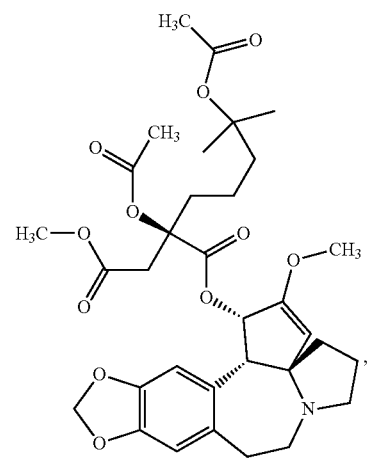
BS-HH-066
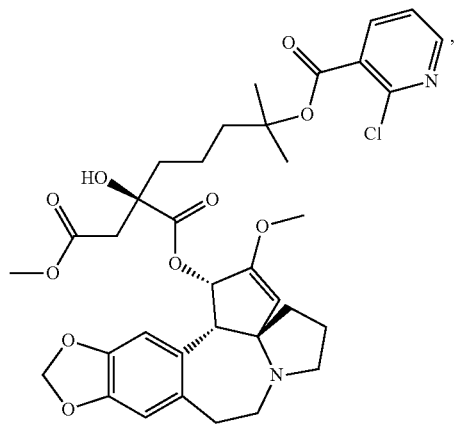
BS-HH-002
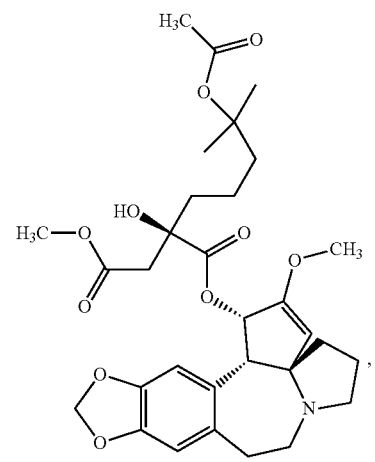
BS-HH-0721
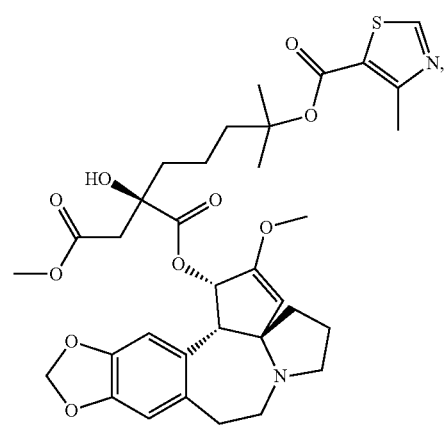
BS-HH-059
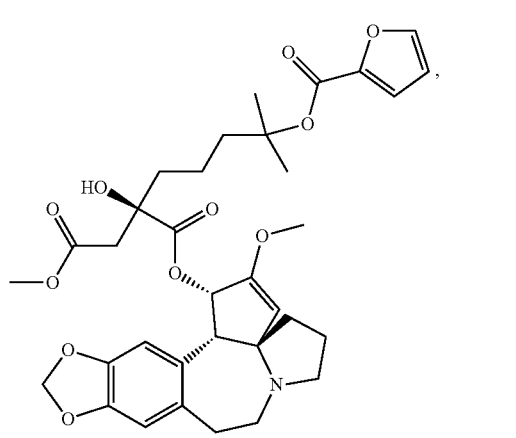
BS-HH-074
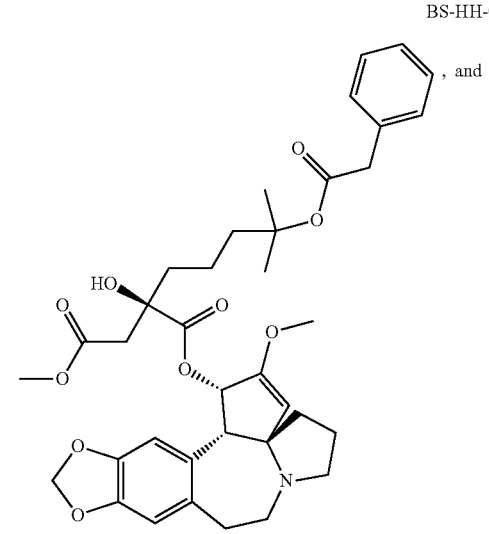

-continued

BS-HH-077

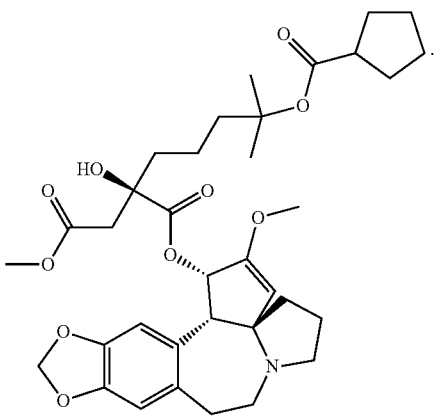

13. A process for preparing the compound of formula (I) according to claim 1, comprising:
    1) subjecting an optionally activated homoharringtonine and an organic acid $R_1CO_2H$ to condensation esterification;
    2) subjecting homoharringtonine and an organic acyl chloride $R_1COCl$ or an organic anhydride $(R_1CO)_2O$ to condensation esterification; or
    3) reacting an activated organic acid $R_1CO_2H$ with homoharringtonine;
    to obtain the compound of formula (I), wherein $R_1$ is as defined in claim 1.

14. A process for preparing the compound of formula (II) according to claim 1, comprising:
    1) subjecting an optionally activated homoharringtonine and an organic acid $R_1CO_2H$ to condensation esterification (wherein $R_1=R_2$) or subjecting an optionally activated compound of formula (I) and an organic acid $R_2CO_2H$ to condensation esterification;
    2) subjecting homoharringtonine and an organic acyl chloride $R_1COCl$ or an organic anhydride $(R_1CO)_2O$ to condensation esterification (wherein $R_1=R_2$), or subjecting the compound of formula (I) and an organic acyl chloride $R_2COCl$ or an organic anhydride $(R_2CO)_2O$ to condensation esterification; or
    3) reacting an activated organic acid $R_1CO_2H$ with homoharringtonine (wherein $R_1=R_2$) or reacting an activated organic acid $R_2CO_2H$ with a compound of formula (I);
    to obtain the compound of formula (II), wherein $R_1$ is as defined in claim 1.

15. A pharmaceutical composition, comprising the acylated homoharringtonine compound of claim 1, or a pharmaceutically acceptable salt thereof, and a pharmaceutically acceptable excipient.

16. A method for treating a subject suffering from tumor, comprising administering to the subject in need thereof an effective amount of the acylated homoharringtonine compound of claim 1, or a pharmaceutically acceptable salt thereof, wherein the tumor is selected from the group consisting of leukemia, multiple myeloma, lymphoma, liver cancer, gastric cancer, breast cancer, cholangiocellular carcinoma, pancreatic cancer, lung cancer, colorectal cancer, osteosarcoma, human cervical cancer, glioma, nasopharyngeal carcinoma, laryngeal carcinoma, esophageal cancer, middle ear tumor, melanoma, and prostate cancer.

* * * * *